(12) United States Patent
Batchelor et al.

(10) Patent No.: US 11,298,183 B2
(45) Date of Patent: Apr. 12, 2022

(54) FIBROID ABLATION POSITIONING DEVICE AND METHODS

(71) Applicant: Gyrus ACMI, Inc., Southborough, MA (US)

(72) Inventors: Kester J. Batchelor, Mound, MN (US); Riyad Moe, Madison, WI (US); Richard Curtis, Maple Grove, MN (US); Nikhil Murdeshwar, Maple Grove, MN (US); Huisun Wang, Maple Grove, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 782 days.

(21) Appl. No.: 15/894,020

(22) Filed: Feb. 12, 2018

(65) Prior Publication Data
US 2018/0161094 A1 Jun. 14, 2018

Related U.S. Application Data

(62) Division of application No. 14/484,438, filed on Sep. 12, 2014, now abandoned.
(Continued)

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 18/1477* (2013.01);
(Continued)

(58) Field of Classification Search
CPC ..... A61B 18/10; A61B 18/12; A61B 18/1206; A61B 18/1266; A61B 18/14;
(Continued)

(56) References Cited

U.S. PATENT DOCUMENTS 5,514,131 A 5/1996 Edwards
5,630,426 A 5/1997 Eggers
(Continued)

FOREIGN PATENT DOCUMENTS

CN 101945618 A 1/2011
CN 103222891 A 7/2013
(Continued)

OTHER PUBLICATIONS

"U.S. Appl. No. 14/484,438, Final Office Action dated Oct. 2, 2017", 7 pgs.
(Continued)

*Primary Examiner* — Khadijeh A Vahdat
(74) *Attorney, Agent, or Firm* — Schwegman Lundberg & Woessner, P.A.

(57) ABSTRACT

A method of treating a patient with a bioelectrical system is provided. The method may include inserting a probe into a first position in an anatomy of the patient, the system being provided with a plurality of electrodes; energizing a first electrode of the plurality of electrodes with a measurement level of power; determining a complex impedance in the patient's anatomy; determining whether the first position is a desired position of the probe for ablating a predetermined portion of tissue of the patient, based on the complex impedance determined; and energizing one of the plurality of electrodes with an ablation level of power, the ablation level of power being greater than the measurement level of power. An apparatus for performing BIA on a patient is also provided.

3 Claims, 15 Drawing Sheets

Related U.S. Application Data

(60) Provisional application No. 61/903,703, filed on Nov. 13, 2013.

(51) Int. Cl.
*A61B 18/00* (2006.01)
*A61B 18/16* (2006.01)

(52) U.S. Cl.
CPC .............. *A61B 2018/00559* (2013.01); *A61B 2018/00577* (2013.01); *A61B 2018/00642* (2013.01); *A61B 2018/00875* (2013.01); *A61B 2018/00904* (2013.01); *A61B 2018/1425* (2013.01); *A61B 2018/162* (2013.01)

(58) Field of Classification Search
CPC ............ A61B 18/1445; A61B 18/1448; A61B 18/1477; A61B 18/1492; A61B 2018/00559; A61B 2018/00577; A61B 2018/00642; A61B 2018/00875; A61B 2018/00904; A61B 2018/1425; A61B 2018/162
USPC ....................................... 606/33–50
See application file for complete search history.

(56) References Cited

U.S. PATENT DOCUMENTS

| | | |
|---|---|---|
| 5,697,909 A | 12/1997 | Eggers |
| 5,730,719 A | 3/1998 | Edwards |
| 6,090,105 A | 7/2000 | Zepeda |
| 6,095,987 A | 8/2000 | Shmulewitz |
| 6,371,926 B1 | 4/2002 | Thorson |
| 6,379,349 B1 | 4/2002 | Mueller |
| 6,572,614 B1 | 6/2003 | Ellman |
| 6,723,094 B1 | 4/2004 | Desinger |
| 6,962,587 B2 | 11/2005 | Johnson |
| 7,179,258 B2 | 2/2007 | Buysse |
| 7,377,918 B2 | 5/2008 | Amoah |
| 7,666,183 B2 | 2/2010 | Desinger |
| 7,854,740 B2 | 12/2010 | Carney |
| 7,862,560 B2 | 1/2011 | Marion |
| 7,918,795 B2 | 4/2011 | Grossman |
| 8,034,049 B2 | 10/2011 | Odom |
| 8,092,449 B2 | 1/2012 | Desinger |
| 8,157,799 B2 | 4/2012 | Desinger |
| 8,216,219 B2 | 7/2012 | Desinger |
| 8,221,406 B2 | 7/2012 | Desinger |
| 2002/0049375 A1 | 4/2002 | Strommer et al. |
| 2003/0045871 A1 | 3/2003 | Jain et al. |
| 2003/0093067 A1 | 5/2003 | Panescu |
| 2003/0109871 A1 | 6/2003 | Johnson et al. |
| 2003/0130711 A1 | 7/2003 | Pearson |
| 2005/0283215 A1 | 12/2005 | Dessinger |
| 2006/0052776 A1 | 3/2006 | Dessinger |
| 2006/0085049 A1 | 4/2006 | Cory |
| 2009/0163904 A1 | 6/2009 | Miller |
| 2009/0171345 A1 | 7/2009 | Miller |
| 2009/0198230 A1 | 8/2009 | Behnke et al. |
| 2010/0024117 A1 | 2/2010 | Fujii |
| 2010/0274239 A1 | 10/2010 | Saurav |
| 2010/0298823 A1 | 11/2010 | Hong |
| 2011/0071516 A1 | 3/2011 | Gregg |
| 2011/0213365 A1 | 9/2011 | Eisele et al. |
| 2011/0230874 A1 | 9/2011 | Epstein |
| 2011/0301591 A1 | 12/2011 | Podhajsky et al. |
| 2012/0323237 A1 | 12/2012 | Saurav |
| 2015/0133911 A1 | 5/2015 | Batchelor et al. |

FOREIGN PATENT DOCUMENTS

| | | |
|---|---|---|
| CN | 105873534 A | 8/2016 |
| EP | 1174093 A1 | 1/2002 |
| EP | 2301462 A1 | 3/2011 |
| EP | 2620113 A1 | 7/2013 |
| EP | 3046494 A1 | 7/2016 |
| JP | 2009518130 A | 5/2009 |
| JP | 2011508628 A | 3/2011 |
| JP | 2011251127 A | 12/2011 |
| JP | 2012504979 A | 3/2012 |
| JP | 2012217856 A | 11/2012 |
| JP | 2013154168 A | 8/2013 |
| JP | 2016537088 A | 12/2016 |
| JP | 6342000 B2 | 5/2018 |
| WO | WO-2015073108 A1 | 5/2015 |

OTHER PUBLICATIONS

"U.S. Appl. No. 14/484,438, Non Final Office Action dated Jun. 12, 2017", 8 pgs.

"U.S. Appl. No. 14/484,438, Response filed Sep. 8, 2017 to Non Final Office Action dated Jun. 12, 2017", 15 pgs.

"U.S. Appl. No. 14/484,438, Response filed Dec. 13, 2016 to Restriction Requirement dated Oct. 18, 2016", 11 pgs.

"U.S. Appl. No. 14/484,438, Restriction Requirement dated Oct. 18, 2016", 39 pgs.

"Chinese Application Serial No. 201480062380.X, Office Action dated Jul. 10, 2018", with English translation of claims, 12 pgs.

"Chinese Application Serial No. 201480062380.X, Office Action dated Oct. 27, 2017", with English translation of claims, 16 pgs.

"Chinese Application Serial No. 201480062380.X, Response filed Mar. 7, 2018 to Office Action dated Oct. 27, 2017", with machine translation, 8 pgs.

"European Application Serial No. 14777972.2, Communication pursuant to Article 94(3) EPC dated Jul. 22, 2019", 4 pgs.

"International Application Serial No. PCT/US2014/055333, International Preliminary Report on Patentability dated May 26, 2016", 7 pgs.

"International Application Serial No. PCT/US2014/055333, International Search Report dated Nov. 20, 2014", 3 pgs.

"International Application Serial No. PCT/US2014/055333, Written Opinion dated Nov. 20, 2014", 5 pgs.

"Japanese Application Serial No. 2016-530119, Decision of Refusal dated Nov. 9, 2017", with English translation of claims, 6 pgs.

"Japanese Application Serial No. 2016-530119, Office Action dated Apr. 17, 2017", with English translation of claims, 6 pgs.

"Japanese Application Serial No. 2016-530119, Response filed Mar. 9, 2018 to Decision of Refusal dated Nov. 9, 2017", with English translation of claims, 4 pgs.

"Japanese Application Serial No. 2016-530119, Response filed Jun. 28, 2017 to Office Action dated Apr. 17, 2017", with machine translation, 8 pgs.

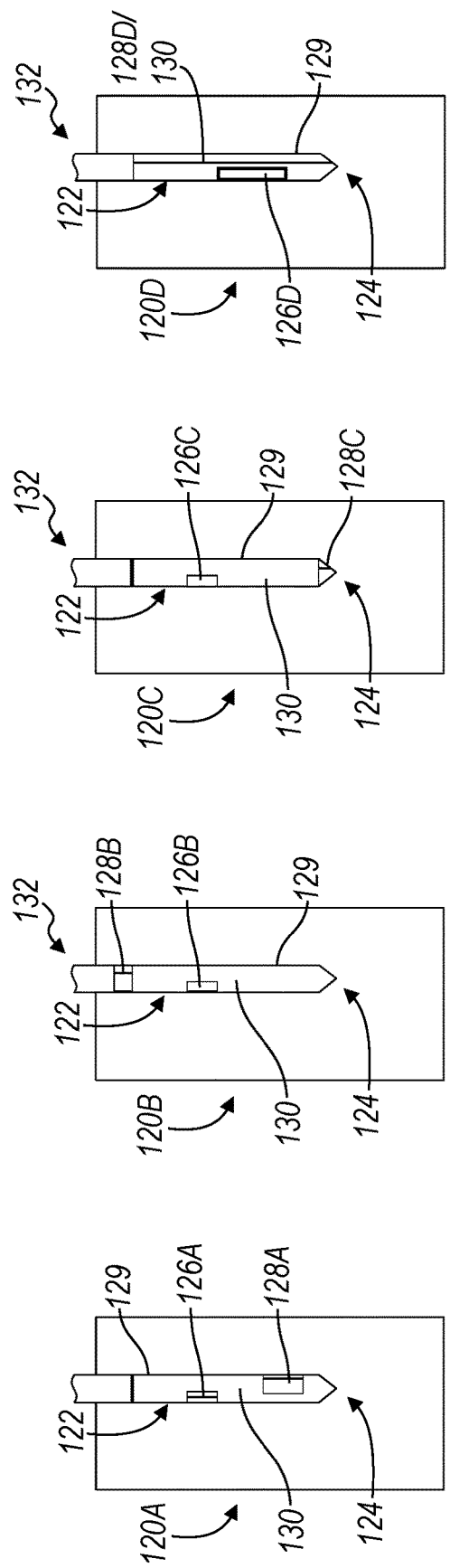
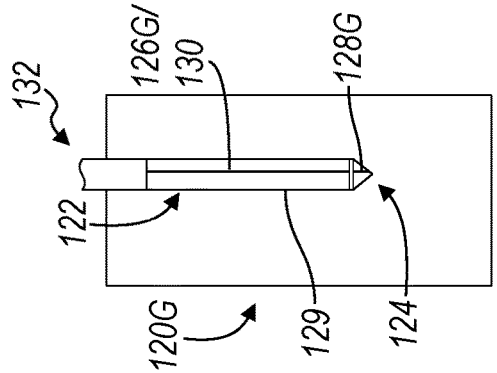
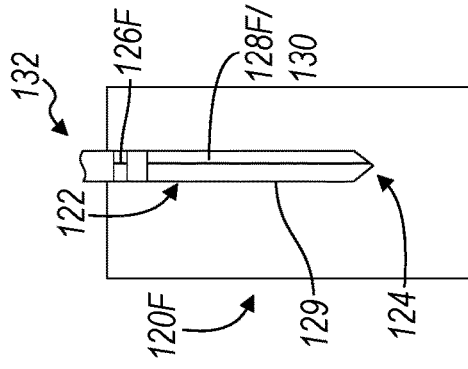
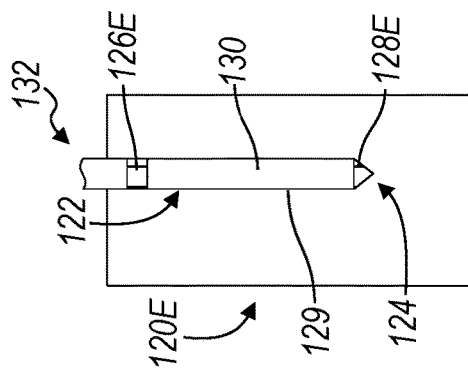

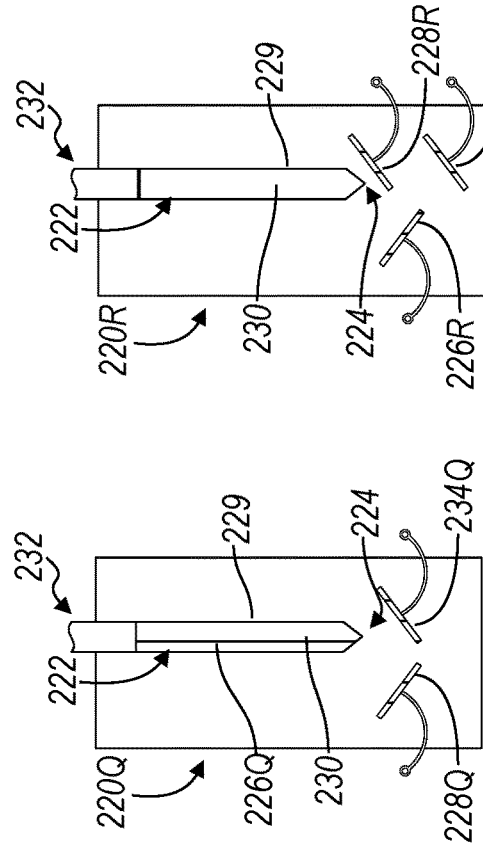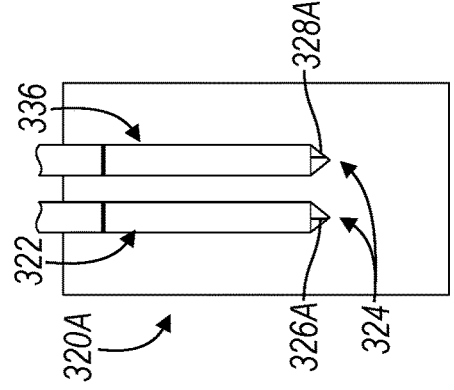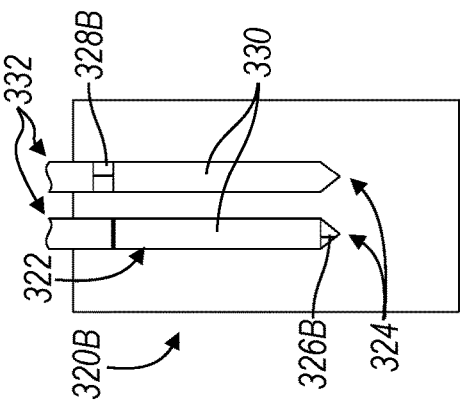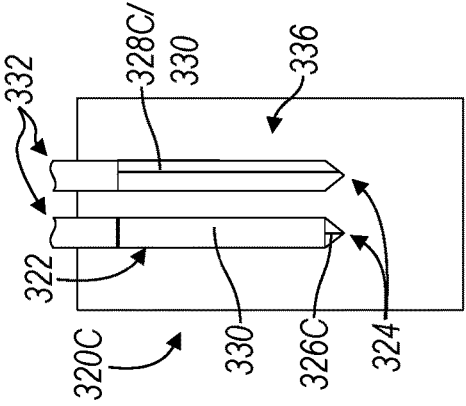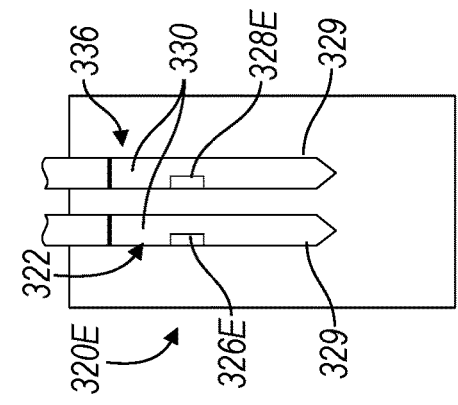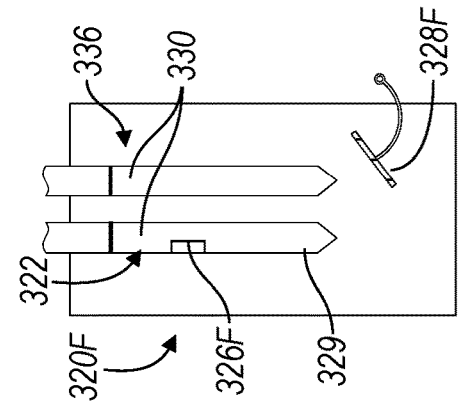

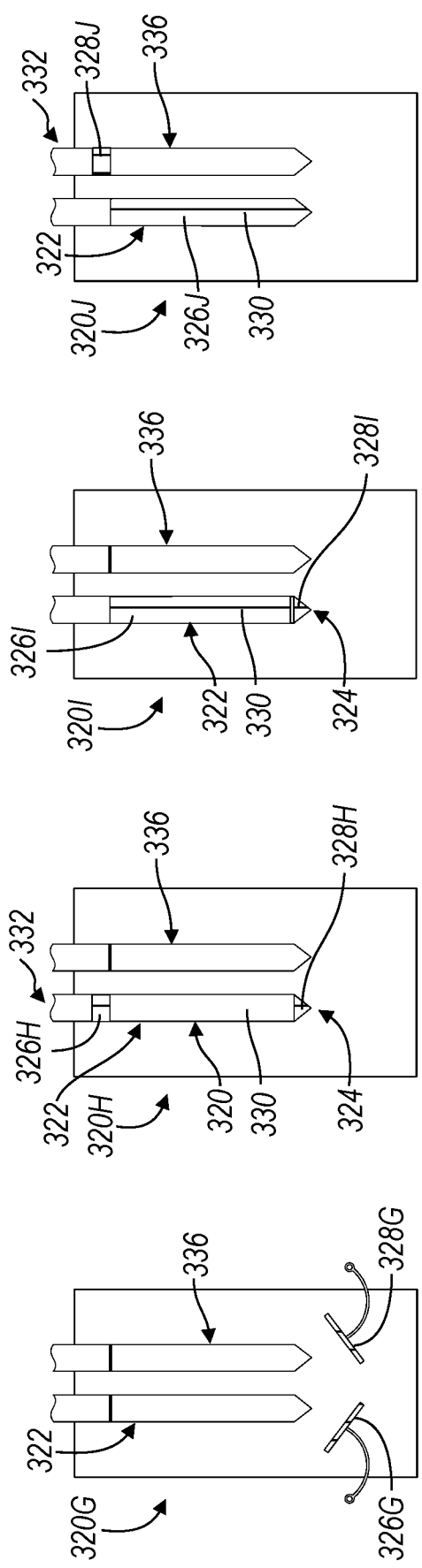
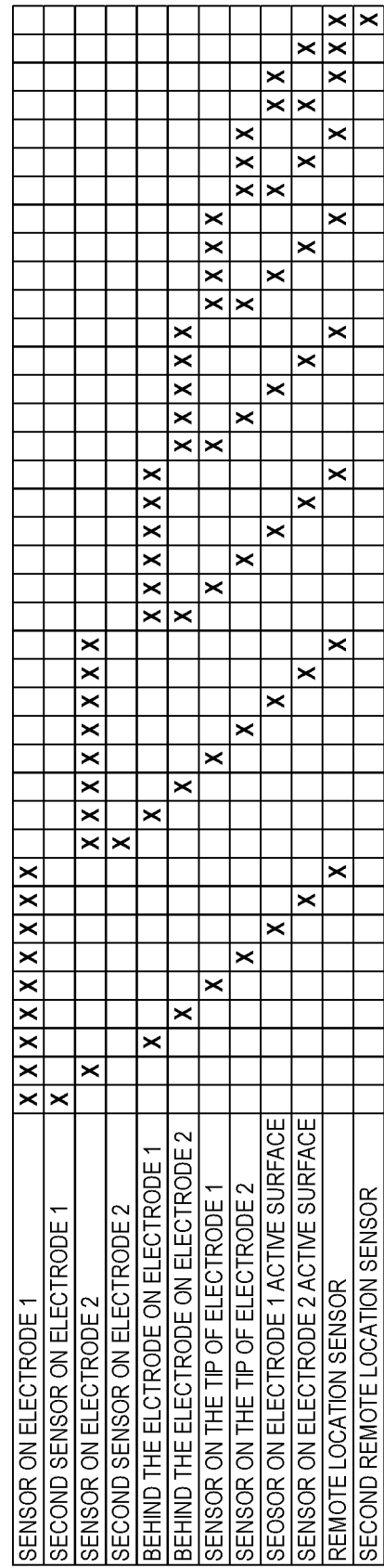

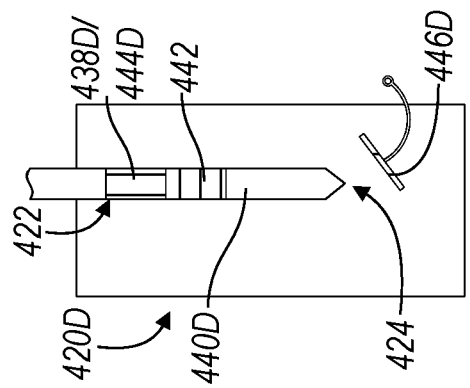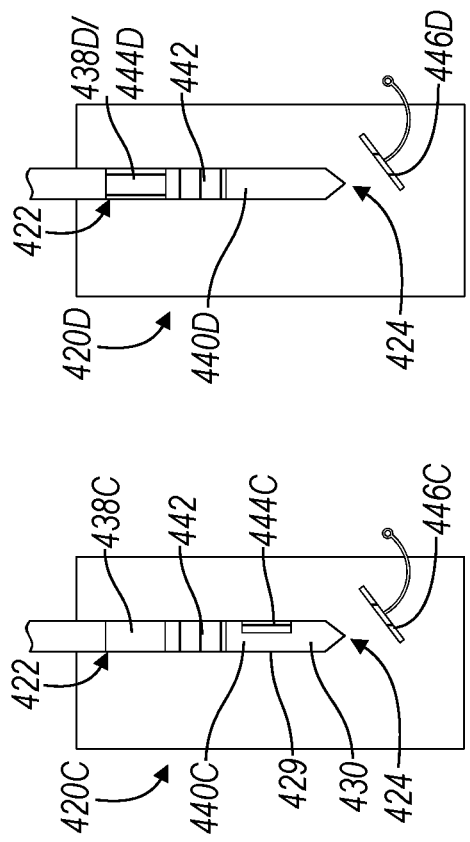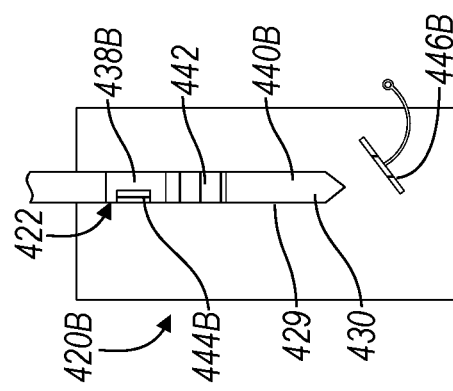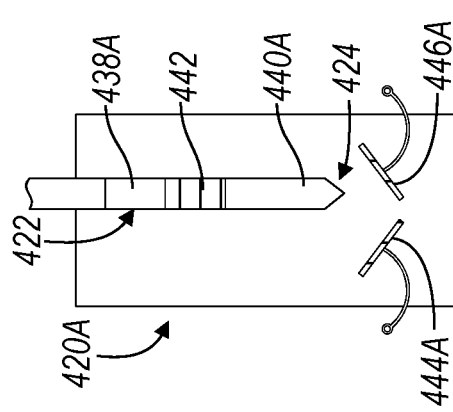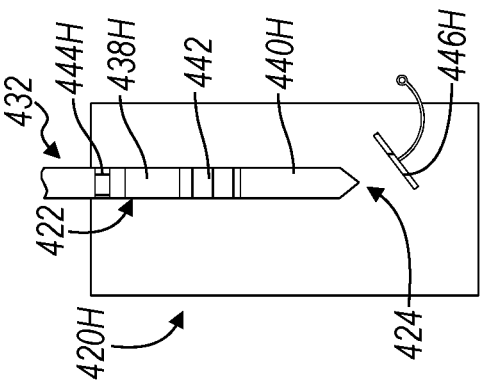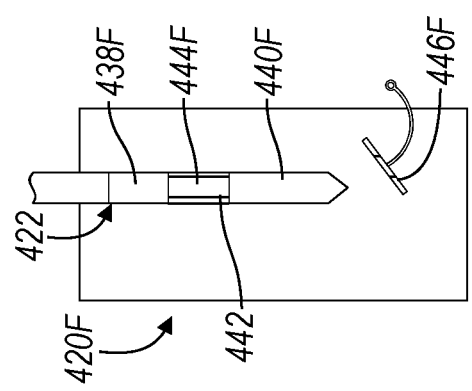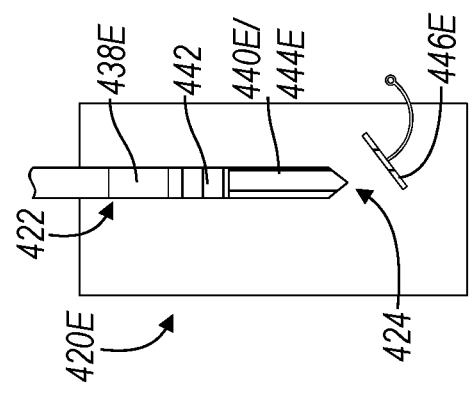

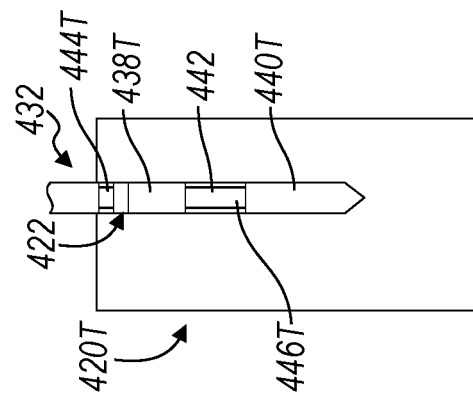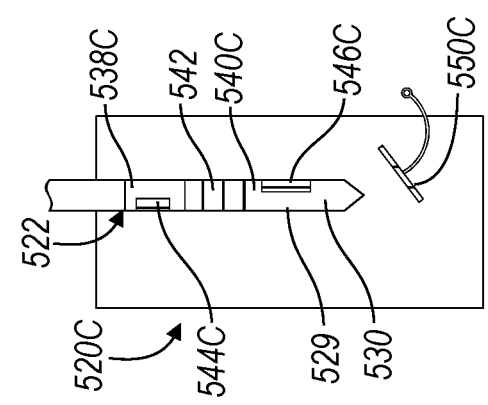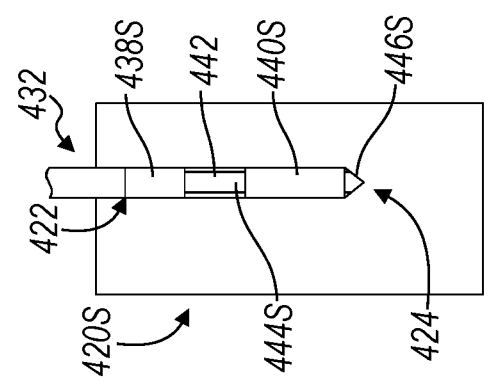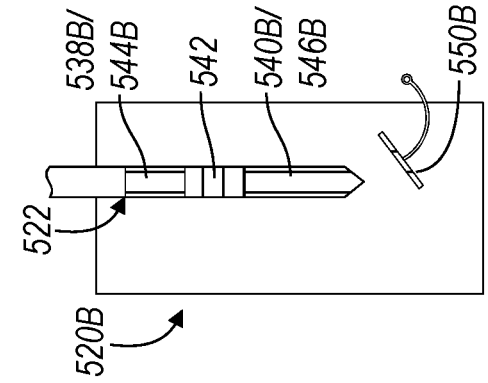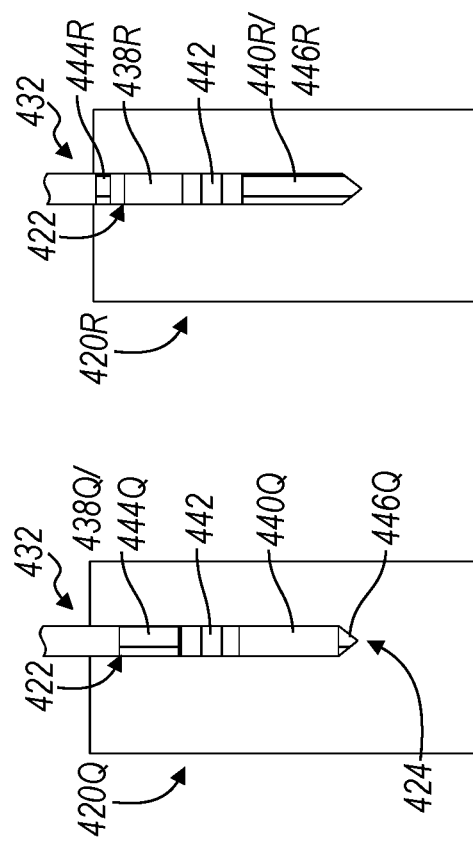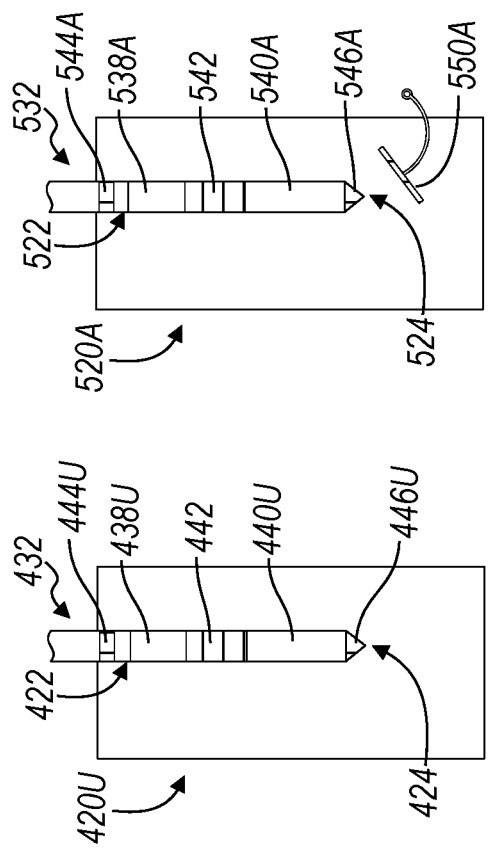

FIG. 8A

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| REMOTE SENSOR 1 | x | x | x | x | x | x | x | x | x | x | x | x | x | x | x | x | x | x | x | x | x | x | x | x | x | x | x | | | | x | |
| REMOTE SENSOR 2 | x | x | x | x | x | x | x | x | | | | | | | | | | | | | | | | | | | | x | x | | x | x |
| REMOTE SENSOR 3 | x | | | | | | | | | | | | | | | | | | | | | | | | | | | | | | | x |
| SENSOR ON ELECTRODE 1 | | x | | | | | x | x | x | x | | | | | | x | x | x | x | | | | | | | | | | | | | |
| SENSOR ON ELECTRODE 2 | | | x | | | x | | | | | x | | | | x | | | | | | | | | | | | | | | | | |
| ELECTRODE 1 ACTS AS SENSOR | | | | x | | | | | x | | | x | | | | | | | | x | x | x | | x | x | | | | | | | |
| ELECTRODE 2 ACTS AS SENSOR | | | | | x | | | | | x | | | x | | | | | x | | | | x | x | | x | | | | | | | |
| SENSOR LOCATED BETWEEN ELECTRODE 1 & 2 | | | | | | x | | | | | x | | | x | x | | | | x | | | | x | | | x | x | | x | | | |
| SENSOR AT THE TIP OF THE NEEDLE | | | | | | | x | | | | | x | x | | | | x | | | | x | | | | | | x | x | | x | | |
| SENSOR LOCATED PROXIMALLY (BEHIND ELECTRODES) | x | | | | | | | x | | | | | | | | | | x | | x | | | | x | | | | | x | x | | x |

FIG. 8B

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| REMOTE SENSOR 1 | x | x | x | x | | | | | | | | | | | | | | | | | | | | | | | | | | | | |
| REMOTE SENSOR 2 | | | | | x | x | x | x | x | x | x | x | x | x | x | | | | | | | | | | | | | | | | | |
| REMOTE SENSOR 3 | | | | | | | | | | | | | | | | x | x | x | x | x | x | x | x | | | | | | | x | x | x |
| SENSOR ON ELECTRODE 1 | | x | | | x | x | x | x | | | | | x | | | x | x | x | x | | | | | x | x | x | | | | x | x | x |
| SENSOR ON ELECTRODE 2 | | | x | | x | x | x | x | | | | x | | x | | x | x | x | x | | | | | x | x | | x | | | x | | x |
| ELECTRODE 1 ACTS AS SENSOR | | | | x | | | | | x | | | | | | | | | | | x | x | x | | | | x | | x | | | | |
| ELECTRODE 2 ACTS AS SENSOR | x | | | | | | | | | x | | | | | x | | | | | | | | x | | | x | | x | | | | |
| SENSOR LOCATED BETWEEN ELECTRODE 1 & 2 | x | x | | | | | | | | | x | x | x | x | x | | | | | | | | | | x | x | x | | | x | x | x |
| SENSOR AT THE TIP OF THE NEEDLE | x | | x | | | | | | | | | | | | | | | | | x | | x | x | | | | | x | x | | x | x |
| SENSOR LOCATED PROXIMALLY (BEHIND ELECTRODES) | x | x | x | | | | | | | | | | | | | | | | | | x | | | | | | | | x | x | x | x |

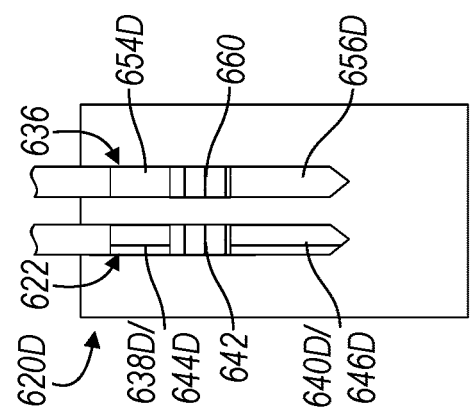
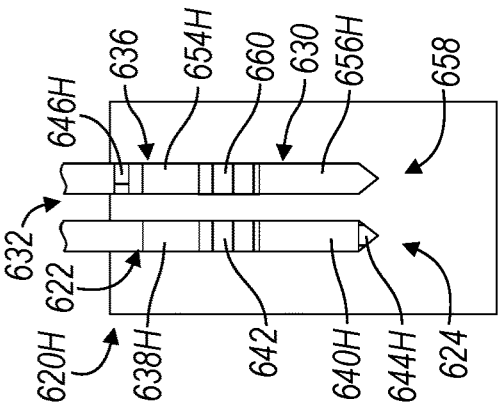
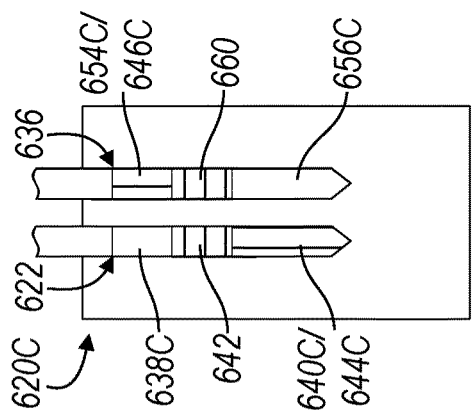
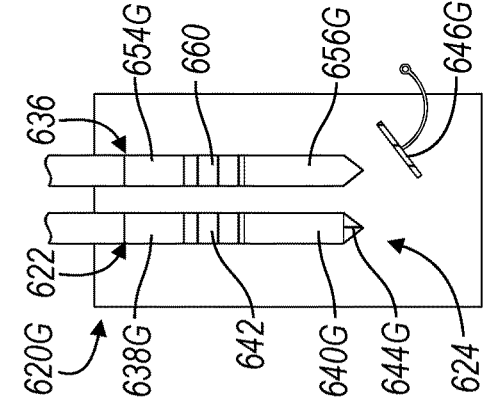
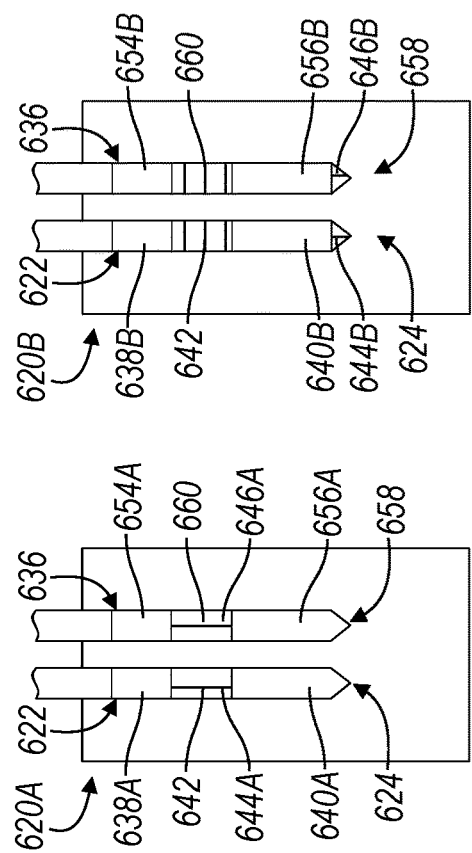
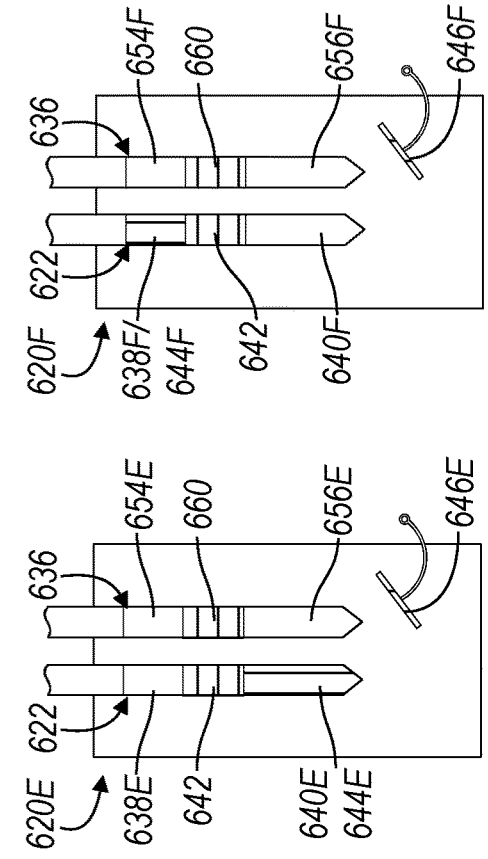

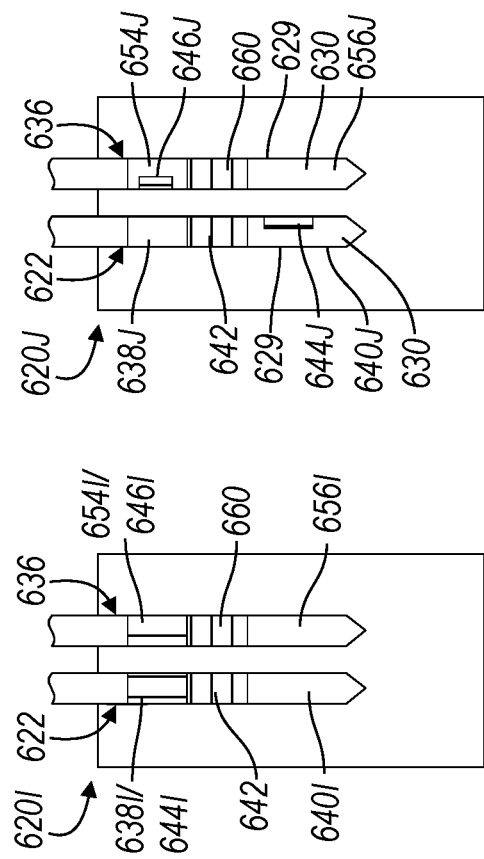
FIG. 9I
FIG. 9J
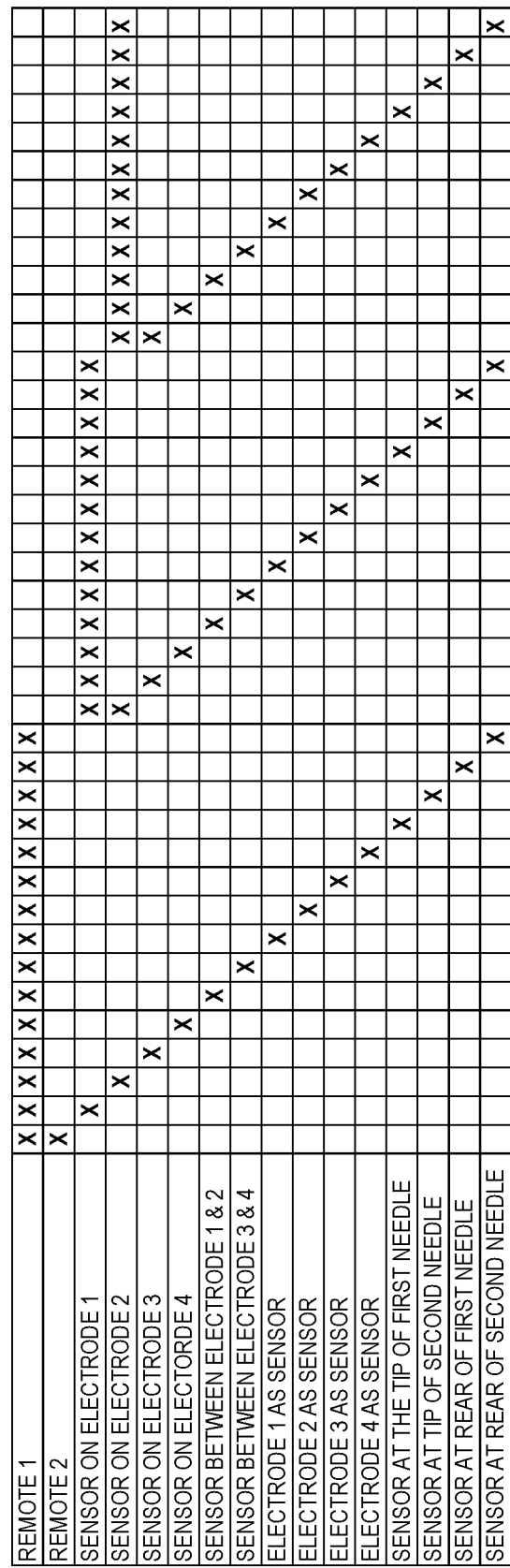
FIG. 10A

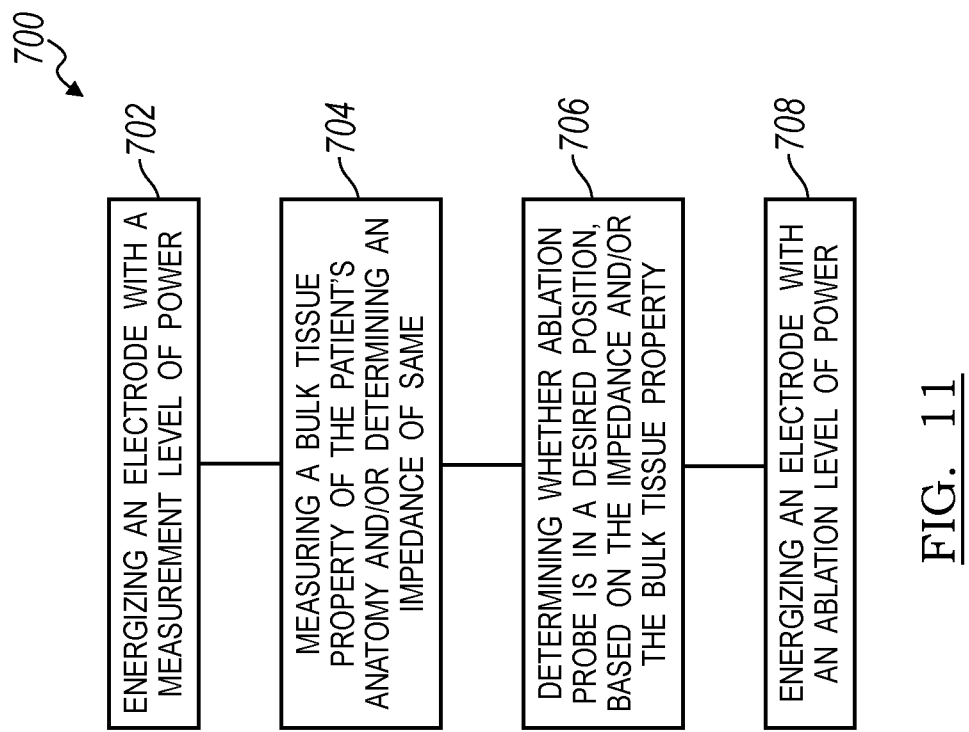

FIBROID ABLATION POSITIONING DEVICE AND METHODS

RELATED APPLICATION

This application is a divisional of U.S. patent application Ser. No. 14/484,438, filed on Sep. 12, 2014, which claims the benefit of U.S. Provisional Patent Application No. 61/903,703, filed on Nov. 13, 2013.

The contents of the above applications are incorporated herein by reference in their entirety.

FIELD

The present disclosure relates to an ablation device, and methods for conducting tissue ablation.

BACKGROUND

The statements in this section merely provide background information related to the present disclosure and may or may not constitute prior art.

Ablation needles are currently used to create large areas of necrotic tissue. They can be used for a number of different surgical applications, for example, base of tongue volume reduction or fibroid and/or tumor ablation.

Proper placement of needle electrodes within tumors, while affecting as little adjacent tissue as possible, is desired. Further, an incorrectly placed ablation electrode could result in less than satisfactory necrosis of the tumor and recurrence of the growth. Correct application of energy and detection of endpoint of energy delivery also ensure appropriate amounts of tissue necrosis.

Current state of the art for these ablative techniques require that additional observational devices be used to ensure that the electrode needle is properly placed within the body tissue, detecting the tissue condition throughout the progression of the tissue modification, and detecting when tissue modification is complete. In areas such as atrial and ventricular catheter ablation, the use of fluoroscopy combined with Bioelectrical Analysis have been considered an additional way to ensure that the ablation catheter is correctly placed against heart tissue, rather than sitting in the patient's blood stream to ensure appropriate ablation of the heart tissue. This has been noted in the following documents: U.S. Pat. No. 7,179,258; US 2009/0163904; US 2010/0274239; US 2010/0298823; US 2012/0323237; and U.S. Pat. No. 7,854,740.

Such additional systems require the surgeon to have detailed knowledge of the use of these visualization systems and have access to them at the time of the procedure. Further, additional capital is required for these advanced systems, which detracts from the overall desirability of needle-based ablation technology.

Accordingly, there is a need for an improved system for locating and/or monitoring tissue for which needle necrosis is desired.

SUMMARY

The present disclosure provides an improved ablation needle, and methods for conducting tissue ablation.

Accordingly, pursuant to one aspect of the invention, there is contemplated a method comprising one or more of the following steps: A method of treating a patient comprising: providing a bioelectrical system comprising a probe and a plurality of electrodes; inserting the probe into a position in an anatomy of the patient; energizing a first electrode of the plurality of electrodes with a measurement level of power, the first electrode being coupled with the probe; measuring a bulk tissue property in the patient's anatomy; determining a complex impedance based on the measured bulk tissue property; determining whether the position is a desired position of the probe for ablating a predetermined portion of tissue in the anatomy, based on the complex impedance determined; energizing an ablation electrode of the plurality of electrodes with an ablation level of power when the probe is in the desired position; delivering a source ablation signal from the ablation electrode when the ablation electrode is energized, wherein the ablation electrode is coupled with the probe, the source ablation signal becoming an ablation return signal; delivering a source measurement signal from the first electrode when the first electrode is energized, the source measurement signal becoming a measurement return signal; receiving the measurement return signal through a second electrode of the plurality of electrodes, the second electrode being provided on a measurement return device that is spaced a distance away from the probe; and receiving the ablation return signal through a third electrode of the plurality of electrodes, the third electrode being provided on an ablation return device that is spaced a distance away from the probe.

The method of treating the patient may be further characterized by one or any combination of the following features: the source ablation signal passes through tissue to the second electrode, the source ablation signal becoming an ablation return signal when the source ablation signal passes through tissue to the second electrode, the method further includes receiving the ablation return signal through the second electrode; and the source ablation signal passes through tissue to the third electrode of the plurality of electrodes, the source ablation signal becoming an ablation return signal when the source ablation signal passes through tissue to the third electrode, the method further includes receiving the ablation return signal through the third electrode.

Accordingly, pursuant to yet another aspect, a method of treating a patient includes one or more of the following steps: providing a bioelectrical system comprising a probe and a plurality of electrodes; inserting the probe into a position in an anatomy of the patient; energizing a first electrode and a second electrode of the plurality of electrodes with a measurement level of power, the first electrode being energized in opposite polarity with respect to the second electrode; determining an impedance in the anatomy; determining whether the position is a desired position of the probe for ablating a predetermined portion of tissue in the anatomy, based on the impedance determined; and energizing two of the plurality of electrodes with an ablation level of power when the probe is in the desired position.

The method of treating the patient may be further characterized by one or any combination of the following features: the method further includes energizing one of the two electrodes in opposite polarity with respect to the other of the two electrodes, the method further includes providing the ablation level of power as greater than the measurement level of power, the step of determining an impedance in the patient's anatomy including determining a complex impedance, providing the two electrodes of the plurality of electrodes as being coupled with the probe, and providing the one of the two electrodes as the first electrode and the other of the two electrodes as the second electrode; the method further includes energizing one of the two electrodes in opposite polarity with respect to the other of the two electrodes, the method further includes providing the ablation level of power as greater than the measurement level of power, the step of determining an impedance in the patient's anatomy including determining a complex impedance, providing the two electrodes of the plurality of electrodes as being coupled with the probe, and providing the two of the plurality of electrodes as being a third electrode and a fourth electrode of the plurality of electrodes; the method further includes providing the first electrode as being coupled with the probe, and delivering a source measurement signal from the first electrode when the first electrode is energized, the source measurement signal becoming a return measurement signal, the method further includes receiving the return measurement signal through the second electrode; the method further includes receiving an ablation return signal through the fourth electrode.

Accordingly, pursuant to yet another aspect, a method of treating a patient with a bioelectrical system includes one or more of the following steps: locating a target object in an anatomy of the patient by performing bioelectrical impedance analysis (BIA) on the anatomy of the patient, including determining a complex impedance in the patient's anatomy; positioning a probe in a desired position for ablating the target object, based on the location of the target object determined by the step of locating the target object; energizing an electrode to an ablation level sufficient to ablate the target object; and providing the electrode as being coupled with the probe.

The method of treating the patient may be further characterized by one or any combination of the following features: the electrode is provided as a first electrode, the method further includes delivering a source ablation signal from the first electrode when the first electrode is energized with the ablation level of power, the method further includes delivering a source measurement signal from the first electrode when first electrode is energized with the measurement level of power, the source measurement signal becoming a measurement return signal, the method further includes receiving the measurement return signal through a second electrode; the method further includes receiving an ablation return signal through the second electrode; and the method further includes receiving an ablation return signal through a third electrode.

Further aspects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1A is a side view of a sensing and ablation system having a single probe in the form of a monopolar ablation needle, in accordance with the principles of the present disclosure;

FIG. 1Ai is a schematic diagram illustrating the principles of complex impedance as understood herein, according to the principles of the present disclosure;

FIG. 2A is a side view of still another sensing and ablation system having a single probe in the form of a monopolar ablation needle, in accordance with the principles of the present disclosure;

FIG. 2B is a side view of still another sensing and ablation system having a single probe in the form of a monopolar ablation needle, in accordance with the principles of the present disclosure;

FIG. 2C is a side view of still another sensing and ablation system having a single probe in the form of a monopolar ablation needle, in accordance with the principles of the present disclosure;

FIG. 2D is a side view of still another sensing and ablation system having a single probe in the form of a monopolar ablation needle, in accordance with the principles of the present disclosure;

FIG. 2E is a side view of still another sensing and ablation system having a single probe in the form of a monopolar ablation needle, in accordance with the principles of the present disclosure;

FIG. 2F is a side view of still another sensing and ablation system having a single probe in the form of a monopolar ablation needle, in accordance with the principles of the present disclosure;

FIG. 2G is a side view of still another sensing and ablation system having a single probe in the form of a monopolar ablation needle, in accordance with the principles of the present disclosure;

FIG. 3Q is a side view of still another sensing and ablation system having a single probe in the form of a monopolar ablation needle, in accordance with the principles of the present disclosure;

FIG. 3R is a side view of still another sensing and ablation system having a single probe in the form of a monopolar ablation needle, in accordance with the principles of the present disclosure;

FIG. 4A is a side view of a sensing and ablation system having two probes in the form of monopolar ablation needles, in accordance with the principles of the present disclosure;

FIG. 4B is a side view of another sensing and ablation system having two probes in the form of monopolar ablation needles, in accordance with the principles of the present disclosure;

FIG. 4C is a side view of yet another sensing and ablation system having two probes in the form of monopolar ablation needles, in accordance with the principles of the present disclosure;

FIG. 4D is a side view of still another sensing and ablation system having two probes in the form of monopolar ablation needles, in accordance with the principles of the present disclosure;

FIG. 4E is a side view of still another sensing and ablation system having two probes in the form of monopolar ablation needles, in accordance with the principles of the present disclosure;

FIG. 4F is a side view of still another sensing and ablation system having two probes in the form of monopolar ablation needles, in accordance with the principles of the present disclosure;

FIG. 4G is a side view of still another sensing and ablation system having two probes in the form of monopolar ablation needles, in accordance with the principles of the present disclosure;

FIG. 4H is a side view of still another sensing and ablation system having two probes in the form of monopolar ablation needles, in accordance with the principles of the present disclosure;

FIG. 4I is a side view of still another sensing and ablation system having two probes in the form of monopolar ablation needles, in accordance with the principles of the present disclosure;

FIG. 4J is a side view of still another sensing and ablation system having two probes in the form of monopolar ablation needles, in accordance with the principles of the present disclosure;

FIG. 5 is a table showing additional variants of a sensing and ablation system having two probes in the form of monopolar ablation needles, in accordance with the principles of the present disclosure;

FIG. 6A is a side view of a sensing and ablation system having a single probe in the form of a bipolar ablation needle, in accordance with the principles of the present disclosure;

FIG. 6B is a side view of another sensing and ablation system having a single probe in the form of a bipolar ablation needle, in accordance with the principles of the present disclosure;

FIG. 6C is a side view of yet another sensing and ablation system having a single probe in the form of a bipolar ablation needle, in accordance with the principles of the present disclosure;

FIG. 6D is a side view of still another sensing and ablation system having a single probe in the form of a bipolar ablation needle, in accordance with the principles of the present disclosure;

FIG. 6E is a side view of still another sensing and ablation system having a single probe in the form of a bipolar ablation needle, in accordance with the principles of the present disclosure;

FIG. 6F is a side view of still another sensing and ablation system having a single probe in the form of a bipolar ablation needle, in accordance with the principles of the present disclosure;

FIG. 6G is a side view of still another sensing and ablation system having a single probe in the form of a bipolar ablation needle, in accordance with the principles of the present disclosure;

FIG. 6H is a side view of still another sensing and ablation system having a single probe in the form of a bipolar ablation needle, in accordance with the principles of the present disclosure;

FIG. 6Q is a side view of still another sensing and ablation system having a single probe in the form of a bipolar ablation needle, in accordance with the principles of the present disclosure;

FIG. 6R is a side view of still another sensing and ablation system having a single probe in the form of a bipolar ablation needle, in accordance with the principles of the present disclosure;

FIG. 6S is a side view of still another sensing and ablation system having a single probe in the form of a bipolar ablation needle, in accordance with the principles of the present disclosure;

FIG. 6T is a side view of still another sensing and ablation system having a single probe in the form of a bipolar ablation needle, in accordance with the principles of the present disclosure;

FIG. 6U is a side view of still another sensing and ablation system having a single probe in the form of a bipolar ablation needle, in accordance with the principles of the present disclosure;

FIG. 7A is a side view of still another sensing and ablation system having a single probe in the form of a bipolar ablation needle, in accordance with the principles of the present disclosure;

FIG. 7B is a side view of still another sensing and ablation system having a single probe in the form of a bipolar ablation needle, in accordance with the principles of the present disclosure;

FIG. 7C is a side view of still another sensing and ablation system having a single probe in the form of a bipolar ablation needle, in accordance with the principles of the present disclosure;

FIG. 8A is a table showing additional variants of a sensing and ablation system having a single probe in the form of a bipolar ablation needle, in accordance with the principles of the present disclosure;

FIG. 8B is a table showing more additional variants of a sensing and ablation system having a single probe in the form of a bipolar ablation needle, in accordance with the principles of the present disclosure;

FIG. 9A is a side view of a sensing and ablation system having two probes in the form of bipolar ablation needles, in accordance with the principles of the present disclosure;

FIG. 9B is a side view of another sensing and ablation system having two probes in the form of bipolar ablation needles, in accordance with the principles of the present disclosure;

FIG. 9C is a side view of yet another sensing and ablation system having two probes in the form of bipolar ablation needles, in accordance with the principles of the present disclosure;

FIG. 9D is a side view of still another sensing and ablation system having two probes in the form of bipolar ablation needles, in accordance with the principles of the present disclosure;

FIG. 9E is a side view of still another sensing and ablation system having two probes in the form of bipolar ablation needles, in accordance with the principles of the present disclosure;

FIG. 9F is a side view of still another sensing and ablation system having two probes in the form of bipolar ablation needles, in accordance with the principles of the present disclosure;

FIG. 9G is a side view of still another sensing and ablation system having two probes in the form of bipolar ablation needles, in accordance with the principles of the present disclosure;

FIG. 9H is a side view of still another sensing and ablation system having two probes in the form of bipolar ablation needles, in accordance with the principles of the present disclosure;

FIG. 9I is a side view of still another sensing and ablation system having two probes in the form of bipolar ablation needles, in accordance with the principles of the present disclosure;

FIG. 9J is a side view of still another sensing and ablation system having two probes in the form of bipolar ablation needles, in accordance with the principles of the present disclosure;

FIG. 10A is a table showing additional variants of a sensing and ablation system having two probes in the form of bipolar ablation needles, in accordance with the principles of the present disclosure;

FIG. 10B is a table showing more additional variants of a sensing and ablation system having two probes in the form of bipolar ablation needles, in accordance with the principles of the present disclosure;

FIG. 10C is a table showing even more additional variants of a sensing and ablation system having two probes in the form of bipolar ablation needles, in accordance with the principles of the present disclosure; and FIG. 11 is a block diagram illustrating a method of treating a patient with a bioelectrical system, in accordance with the principles of the present disclosure.

DETAILED DESCRIPTION

The following description is merely exemplary in nature and is not intended to limit the present disclosure, application, or uses.

The present disclosure provides a tissue ablation device, system, and method. Various forms of a needle ablation electrode and system are disclosed. Each system has a sensing circuit and an ablation circuit. The sensing circuit is configured to send a measurement signal into a patient's tissue and to measure a bulk tissue property and/or determine impedance, in order to decide whether the probe has been properly placed. Once the probe is properly placed, the tissue can be ablated with the ablation circuit.

Figure 1A:
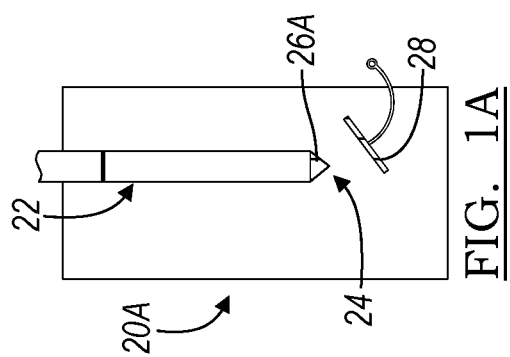
FIG. 1B is a side view of another sensing and ablation system having a single probe in the form of a monopolar ablation needle, in accordance with the principles of the present disclosure.
FIG. 1C is a side view of yet another sensing and ablation system having a single probe in the form of a monopolar ablation needle, in accordance with the principles of the present disclosure.
FIG. 1D is a side view of still another sensing and ablation system having a single probe in the form of a monopolar ablation needle, in accordance with the principles of the present disclosure.

For example, with reference to FIG. 1A, a sensing and ablation system for treating a patient through bioelectricity is illustrated and generally designated at 20A. The system 20A includes a probe 22 in the form of a needle having a pointed distal end 24. The probe 22 is configured to be inserted into the patient's anatomy for ablation of bodily tissue in the patient's anatomy. The probe 22 may be rigid, malleable, or selectively deflectable.

The probe 22 is itself a monopolar ablation electrode that is configured to emit an electric signal for ablation of nearby tissue. Accordingly, the probe 22 is typically placed near tissue for which necrosis or other ablation is desired. As used herein (unless otherwise described), the term "monopolar" denotes an apparatus bearing an electrode configured to emit an electric signal to pass to a return electrode, wherein the return electrode is located remotely from, or spaced a distance away from the apparatus. As used herein, unless otherwise described, "bipolar" refers to an ablation circuit located on a probe apparatus, wherein each of the electrodes of the bipolar circuit is coupled with the probe apparatus. In the "bipolar" circuit, a signal is sent between two electrodes that are both coupled to a probe device and both are inserted into the patient on the device.

The probe 22 has a first electrode 26A attached to the distal end 24 of the probe 22. The first electrode 26A is an active electrode that is coupled with and energized by an electrode energy source. When energized, the power is applied to the electrode. A skin patch electrode 28 in this example is located on the patient's skin (not shown). The first electrode 26A and the patch electrode 28 make up a sensing circuit. The patch electrode 28 is a neutral electrode that is not configured to be energized by an energy source. In other words, the patch electrode 28 is grounded, or electrically tied to earth.

The patch electrode 28 is configured to receive a measurement signal from the first electrode 26A and conduct data from the measurement signal to determine a complex impedance in the patient's anatomy while the first electrode 26A is energized. For example, the magnitude of the impedance may be calculated from voltage drop and current. For example, the magnitude of the impedance (or the resistance) is equal to the applied voltage drop divided by the current. Reactance may be calculated based on the frequency and capacitance. The phase angle may be determined based on the relationship between the resistance and the reactance. Different tissues have different electrical impedances and resistances, and as such, a user can know whether the probe 22 is appropriately placed, based on the data collected from the sensing circuit.

In one variation, an impedance, such as a complex impedance is determined based on the bulk tissue property or properties measured, such as resistance, reactance, capacitance, and/or inductance. A complex impedance includes resistance and reactance. For example, see FIG. 1Ai. FIG. 1Ai illustrates the complex nature of the complex impedance Z. The complex impedance Z is a measure of the overall opposition of a circuit to current, or how much the circuit impedes the flow of current. The complex impedance Z takes into account the effects of capacitance and inductance. The effects of capacitance and inductance vary with the frequency of the current passing through the circuit, and as such, complex impedance Z varies with frequency. The complex impedance Z has a constant component, which may be referred to as Resistance R, or simple impedance. The complex impedance Z also has a Reactance X component, which is the part that varies with frequency due to capacitance and inductance. Total Reactance X is the difference between Capacitive Reactance $X_C$ and Inductive Reactance $X_L$. The capacitance and inductance cause a phase shift between the current and voltage. Thus, to determine the complex impedance Z, the simple impedance, or resistance, R and the Reactance X must be added as vectors at right angles, as illustrated in FIG. 1Ai. Accordingly, Complex Impedance Z equals the square root of the sum of the Resistance R squared and the Reactance X squared, or $Z=\sqrt{R^2+X^2}$.

The sensing and ablation system 20A also includes an ablation circuit, made up of the probe 22 itself and the patch electrode 28, or another electrode. In the alternative, the ablation circuit may also include the first electrode 26A. The ablation circuit is configured to deliver a source ablation signal from the probe 22 (or from the first electrode 26, located on the probe 22). The probe 22 (or first electrode 26) is configured to deliver the source ablation signal to the patient's tissue, and the source ablation signal is configured to travel through the tissue and become an ablation return signal. The ablation circuit is configured to receive the ablation return signal on the patch electrode 28 (or another electrode) that is disposed a distance away from the probe 22. Thus, the patch electrode 28 receives the ablation return signal as the tissue is ablated by the ablation circuit. The power of the ablation signal is higher than the power of the measurement signal. Accordingly, the measurement signal preferably does not alter the tissue; however, the ablation signal preferably causes necrosis of the tissue.

Figure 1B:
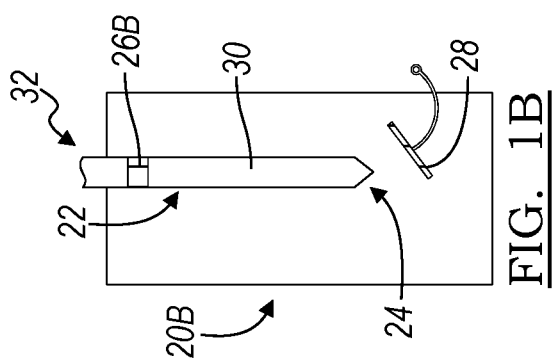

Referring now to FIG. 1B, a variation from the sensing and ablation system illustrated in FIG. 1A at reference number 20A is now illustrated at reference number 20B. The sensing and ablation system 20B shown in FIG. 1B may be the same as the sensing and ablation system 20A illustrated in FIG. 1A, except that the first electrode 26B is illustrated behind the needle portion 30 of the probe 22. In other words, the first electrode 26B is located proximally of the needle portion 30, or closer to a proximal end 32 of the probe 22 than the needle portion 30.

Figure 1C:
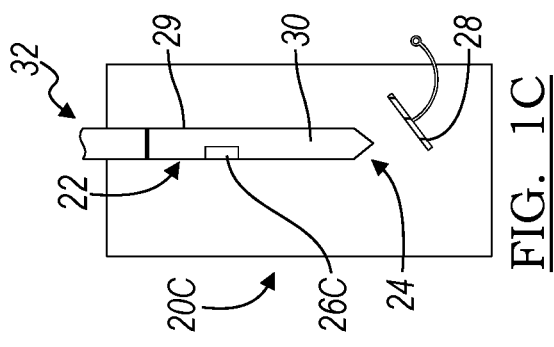

Referring now to FIG. 1C, a variation from the sensing and ablation system illustrated in FIGS. 1A and 1B at reference numbers 20A and 20B is now illustrated at reference number 20C. The sensing and ablation system 20C shown in FIG. 1C may be the same as the sensing and ablation system 20A or 20B illustrated in FIG. 1A or 1B, except that the first electrode 26C is illustrated on the side 29 of the needle portion 30 of the probe 22.

Figure 1D:
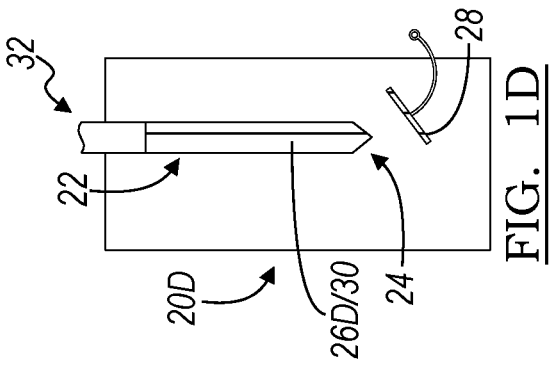
Figure 1A:
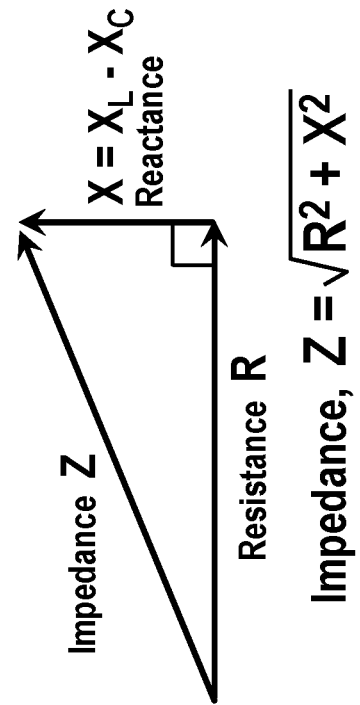

Referring now to FIG. 1D, a variation from the sensing and ablation system illustrated in FIGS. 1A, 1B, and 1C at reference numbers 20A, 20B, and 20C is now illustrated at reference number 20D. The sensing and ablation system 20D shown in FIG. 1D may be the same as the sensing and ablation system 20A, 20B, or 20C illustrated in FIG. 1A, 1B, or 1C, except that the first electrode 26D is illustrated as the needle portion 30 of the probe itself 22.

In another variation, a sensing and ablation system is illustrated in FIG. 2A and generally indicated reference number 120A. In this variation, both a first electrode 126A and a second electrode 128A are located on a probe 122, which is in the form of a needle having a pointed distal end 124. Like the probe 22 of FIGS. 1A-1D, the probe 122 of FIG. 2A is configured to be inserted into the patient's anatomy for ablation of bodily tissue in the patient's anatomy, and the probe 122 itself is a monopolar ablation electrode.

The first and second electrodes 126A, 128A are each attached to the side 129 of the needle portion 130 of the probe 122, and the first and second electrodes 126A, 128A are spaced a distance apart from each other along the length of the side 129 of the needle portion 130. The first electrode 126A and the second electrode 128A make up a sensing circuit. One of the first and second electrodes 126A, 128A is an active electrode that is coupled with and energized by an electrode energy source. The other of the first and second electrodes 126A, 128A is a measurement return electrode, which is a neutral electrode that is not configured to be energized by an energy source. The measurement return electrode is configured to provide data to the system based on the measurement signal, for determining a complex impedance in the patient's anatomy while the active electrode is energized, as explained above. Thus, the measurement signal is passed between the first and second electrodes 126A, 128A.

The sensing and ablation system 120A also includes an ablation circuit, made up of the probe 122 (or one of the electrodes 126A, 128A) and another electrode, such as a skin patch electrode (not shown). The ablation circuit is configured to deliver a source ablation signal from the probe 122 or one of the first and second electrodes 126A, 128A, which is the ablation active electrode. The ablation active electrode is configured to deliver the source ablation signal to the patient's tissue, and the source ablation signal is configured to travel through the tissue and become an ablation return signal. The ablation circuit is configured to receive the ablation return signal through the ablation return electrode, which may be a skin patch electrode (not shown), by way of example. Although not shown in FIG. 2A, skin patches 28 are schematically illustrated in FIGS. 1A-1D, which may be used in conjunction with the system 120A of FIG. 2A. A skin patch may be attached externally to a patient's skin, by way of example. Thus, the ablation return electrode receives the ablation return signal as the tissue is ablated by the ablation circuit.

Referring now to FIG. 2B, a variation from the sensing and ablation system illustrated in FIG. 2A at reference number 120A is now illustrated at reference number 120B. The sensing and ablation system 120B shown in FIG. 2B may be the same as the sensing and ablation system 120A illustrated in FIG. 2A, except that the second electrode 128B is illustrated behind the needle portion 130 of the probe 122. In other words, the second electrode 128B is located proximally of the needle portion 130, or closer to a proximal end 132 of the probe 122 than the needle portion 130 is to the proximal end 132.

Referring now to FIG. 2C, a variation from the sensing and ablation system illustrated in FIGS. 2A and 2B at reference numbers 120A and 120B is now illustrated at reference number 120C. The sensing and ablation system 120C shown in FIG. 2C may be the same as the sensing and ablation system 120A or 120B illustrated in FIG. 2A or 2B, except that the second electrode 128C is illustrated on the distal end 124 of the needle portion 130 of the probe 122.

Referring now to FIG. 2D, a variation from the sensing and ablation system illustrated in FIGS. 2A, 2B, and 2C at reference numbers 120A, 120B, and 120C is now illustrated at reference number 120D. The sensing and ablation system 120D shown in FIG. 2D may be the same as the sensing and ablation system 120A, 120B, or 120C illustrated in FIG. 2A, 2B, or 2C, except that the second electrode 128D is illustrated as the needle portion 130 of the probe itself 122.

Referring now to FIG. 2E, a variation from the sensing and ablation system illustrated in FIGS. 2A-2D at reference numbers 120A-120D is now illustrated at reference number 120E. The sensing and ablation system 120E shown in FIG. 2E may be the same as the sensing and ablation system 120A-120D illustrated in FIGS. 2A-2D, except that the second electrode 128E is illustrated on the distal end 124 of the needle portion 130 of the probe 122 and the first electrode 126E is located proximally of the needle portion 130, or closer to a proximal end 132 of the probe 122 than the needle portion 130 is to the proximal end 132.

Referring now to FIG. 2F, a variation from the sensing and ablation system illustrated in FIGS. 2A-2E at reference numbers 120A-120E is now illustrated at reference number 120F. The sensing and ablation system 120F shown in FIG. 2F may be the same as the sensing and ablation system 120A-120E illustrated in FIGS. 2A-2E, except that the first electrode 126F is located proximally of the needle portion 130, or closer to a proximal end 132 of the probe 122 than the needle portion 130 is to the proximal end 132, and the second electrode 128F is illustrated as the needle portion 130 of the probe itself 122.

Referring now to FIG. 2G, a variation from the sensing and ablation system illustrated in FIGS. 2A-2F at reference numbers 120A-120F is now illustrated at reference number 120G. The sensing and ablation system 120G shown in FIG. 2G may be the same as the sensing and ablation system 120A-120F illustrated in FIGS. 2A-2F, except that the first electrode 126G is illustrated as the needle portion 130 of the probe itself 122 and the second electrode 128G is illustrated on the distal end 124 of the needle portion 130 of the probe 122.

Figure 3D:
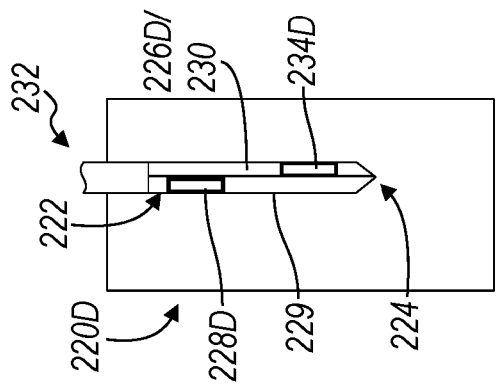
FIG. 3D is a side view of still another sensing and ablation system having a single probe in the form of a monopolar ablation needle, in accordance with the principles of the present disclosure.
Figure 3C:
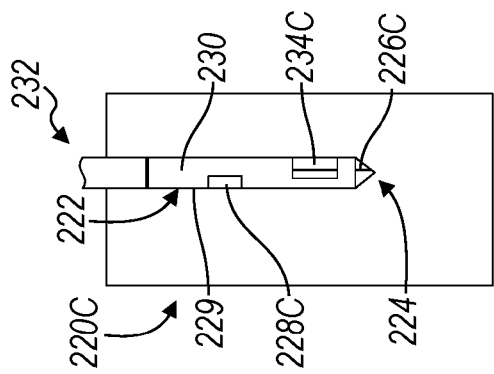
FIG. 3C is a side view of still another sensing and ablation system having a single probe in the form of a monopolar ablation needle, in accordance with the principles of the present disclosure.

FIGS. 1A-2G illustrated a sensing and ablation system that had only two electrodes for the sensing circuit. Referring now to FIG. 3A, a sensing and ablation system is illustrated and generally designated reference number 220A. In this variation, both a first electrode 226A and a second electrode 228A are located on a probe 222, which is in the form of a needle having a pointed distal end 224. Similar to the probes 22, 122 described above, the probe 222 is an electrode for an ablation circuit. In addition to the first electrode 226A, the second electrode 228A, and the probe 222 as an electrode, a third sensing electrode 234A is also provided on the probe 222. Like the probes 22, 122 of FIGS. 1A-2G, the probe 222 of FIG. 3A is configured to be inserted into the patient's anatomy for ablation of bodily tissue in the patient's anatomy.

The first, second, and third electrodes 226A, 228A, 234A are each attached to the side 229 of the needle portion 230 of the probe 222, and each of the first, second, and third electrodes 226A, 228A, 234A are spaced a distance apart from each other along the length of the side 229 of the needle portion 230. Two of the first electrode 226A, the second electrode 228A, and the third electrode 234A make up a sensing circuit. Thus, one of the first, second, and third electrodes 226A, 228A, 234A is an active electrode that is coupled with and energized by an electrode energy source. Another of the first electrode 226A, the second electrode 228A, and the third electrode 234A is a neutral electrode that is not configured to be energized by an energy source; the neutral electrode is configured to provide data based on the measurement signal, for determining a complex impedance in the patient's anatomy while the active electrode is energized, as explained above. (In some variations, an active electrode may also serve as a return electrode). Thus, the measurement signal is passed between two of the first, second, and third electrodes 226A, 228A, 234A.

The sensing and ablation system 220A also includes an ablation circuit, made up of the probe 222 itself (or one of the first, second, or third electrodes 226A, 228A, 234A) and a return electrode (not shown), such as the skin patch electrodes 28 previously described. The ablation circuit is configured to deliver a source ablation signal from an ablation source electrode. The ablation source electrode is configured to deliver the source ablation signal to the patient's tissue, and the source ablation signal is configured to travel through the tissue and become an ablation return signal. The ablation circuit is configured to receive the ablation return signal through an ablation return electrode (not shown). Thus, the ablation return electrode receives the ablation return signal as the tissue is ablated by the ablation circuit.

With the variation of FIG. 3A, the measurement source electrode and the ablation source electrode may be the same electrode of the first, second, and third electrodes 226A, 228A, 234A, but they may also be two different electrodes of the first, second, and third electrodes 226A, 228A, 234A and the probe 222. Similarly, the measurement return electrode and the ablation return electrode may be the same of the first, second, and third electrodes 226A, 228A, 234A, or the ablation return electrode may be another electrode (not shown), for example, a skin patch electrode such as illustrated in FIG. 3H, 3J, 3K, or 3M-3R.

Since the measurement circuit has three electrodes 226A, 228A, 234A, two at a time may be used to sense the voltage drop in different areas, for a more fine-tuned estimate of the position of the probe 222. The measurement circuit may switch between which two of the sensing electrodes 226A, 228A, 234A are used.

Figure 3B:
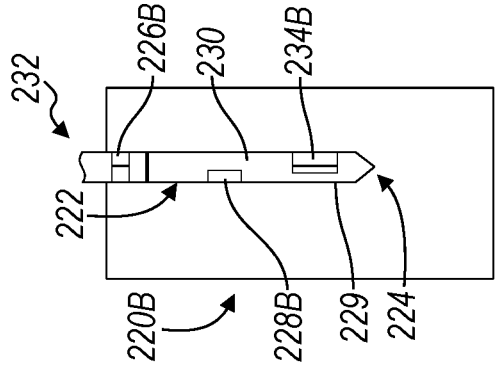
FIG. 3B is a side view of still another sensing and ablation system having a single probe in the form of a monopolar ablation needle, in accordance with the principles of the present disclosure.
Figure 3A:
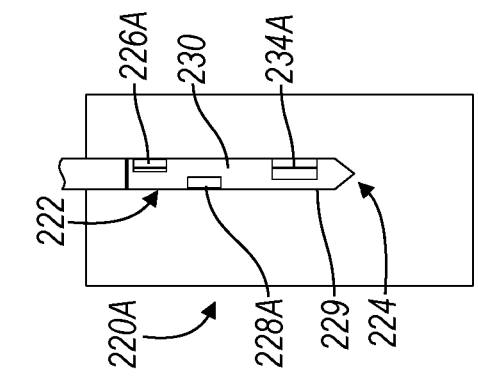
FIG. 3A is a side view of still another sensing and ablation system having a single probe in the form of a monopolar ablation needle, in accordance with the principles of the present disclosure.

Referring now to FIG. 3B, a variation from the sensing and ablation system illustrated in FIG. 3A at reference number 120A is now illustrated at reference number 220B. The sensing and ablation system 220B shown in FIG. 3B may be the same as the sensing and ablation system 220A illustrated in FIG. 3A, except that the first electrode 226B is illustrated behind the needle portion 230 of the probe 222. In other words, the first electrode 226B is located proximally of the needle portion 230, or closer to a proximal end 232 of the probe 222 than the needle portion 230 is to the proximal end 232. The second and third electrodes 228B, 234B are disposed on the side 229 of the probe 222.

Referring now to FIG. 3C, a variation from the sensing and ablation system illustrated in FIGS. 3A and 3B at reference numbers 220A and 220B is now illustrated at reference number 220C. The sensing and ablation system 220C shown in FIG. 3C may be the same as the sensing and ablation system 220A or 220B illustrated in FIG. 3A or 3B, except that the first electrode 226C is illustrated on the distal end 224 of the needle portion 230 of the probe 222. The second and third electrodes 228C, 234C are disposed on the side 229 of the probe 222.

Referring now to FIG. 3D, a variation from the sensing and ablation system illustrated in FIGS. 3A, 3B, and 3C at reference numbers 220A, 220B, and 220C is now illustrated at reference number 220D. The sensing and ablation system 220D shown in FIG. 3D may be the same as the sensing and ablation system 220A, 220B, or 220C illustrated in FIG. 3A, 3B, or 3C, except that the first electrode 226D is illustrated as the needle portion 230 of the probe itself 222. The second and third electrodes 228D, 234D are disposed on the side 229 of the probe 222.

Figure 3H:
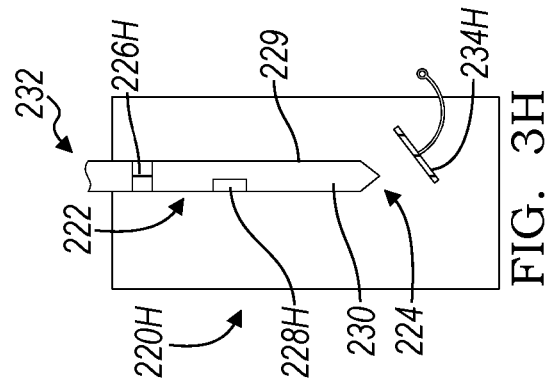
FIG. 3H is a side view of still another sensing and ablation system having a single probe in the form of a monopolar ablation needle, in accordance with the principles of the present disclosure.
Figure 3G:
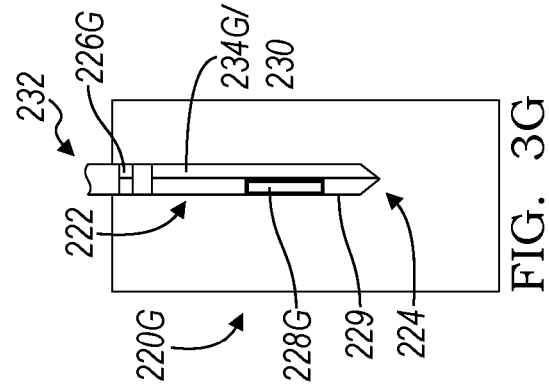
FIG. 3G is a side view of still another sensing and ablation system having a single probe in the form of a monopolar ablation needle, in accordance with the principles of the present disclosure.
Figure 3F:
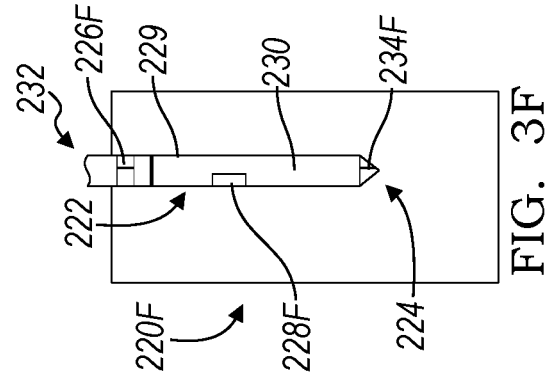
FIG. 3F is a side view of still another sensing and ablation system having a single probe in the form of a monopolar ablation needle, in accordance with the principles of the present disclosure.
Figure 3E:
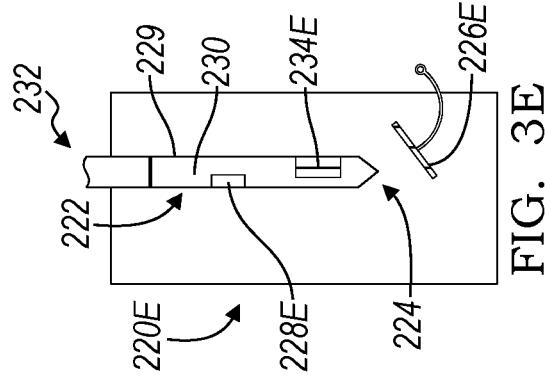
FIG. 3E is a side view of still another sensing and ablation system having a single probe in the form of a monopolar ablation needle, in accordance with the principles of the present disclosure.

Referring now to FIG. 3E, a variation from the sensing and ablation system illustrated in FIGS. 3A-3D at reference numbers 220A-220D is now illustrated at reference number 220E. The sensing and ablation system 220E shown in FIG. 3E may be the same as the sensing and ablation system 220A-220D illustrated in FIGS. 3A-3D, except that the first electrode 226E is a patch electrode located a distance away from the probe 222. The second and third electrodes 228E, 234E are disposed on the side 229 of the probe 222.

Referring now to FIG. 3F, a variation from the sensing and ablation system illustrated in FIGS. 3A-3E at reference numbers 220A-220E is now illustrated at reference number 220F. The sensing and ablation system 220F shown in FIG. 3F may be the same as the sensing and ablation system 220A-220E illustrated in FIGS. 3A-3E, except that the first electrode 226F is located proximally of the needle portion 230, or closer to a proximal end 232 of the probe 222 than the needle portion 230 is to the proximal end 232, and the third electrode 234F is located on the distal end 224 of the probe 222. The second electrode 228F is disposed on the side 229 of the probe 222.

Referring now to FIG. 3G, a variation from the sensing and ablation system illustrated in FIGS. 3A-3F at reference numbers 220A-220F is now illustrated at reference number 220G. The sensing and ablation system 220G shown in FIG. 3G may be the same as the sensing and ablation system 220A-220F illustrated in FIGS. 3A-3F, except that the first electrode 226G is located proximally of the needle portion 230, or closer to a proximal end 232 of the probe 222 than the needle portion 230 is to the proximal end 232, the second electrode 228G is disposed on the side 229 of the probe 222, and the third electrode 234G is the needle 230 itself.

Referring now to FIG. 3H, a variation from the sensing and ablation system illustrated in FIGS. 3A-3G at reference numbers 220A-220G is now illustrated at reference number 220H. The sensing and ablation system 220H shown in FIG. 3H may be the same as the sensing and ablation system 220A-220G illustrated in FIGS. 3A-3G, except that the first electrode 226H is located proximally of the needle portion 230, or closer to a proximal end 232 of the probe 222 than the needle portion 230 is to the proximal end 232, the second electrode 228H is disposed on the side 229 of the probe 222, and the third electrode 234H is a patch electrode disposed a distance away from the distal end 224 of the probe 222.

Figure 3I:
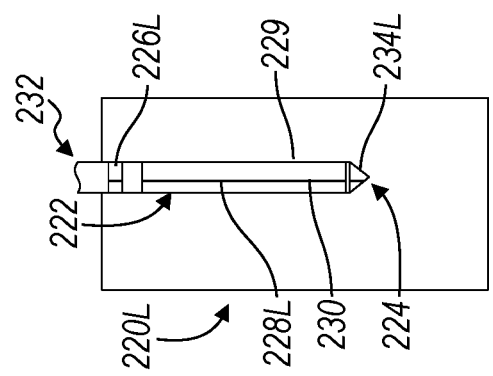
FIG. 3I is a side view of still another sensing and ablation system having a single probe in the form of a monopolar ablation needle, in accordance with the principles of the present disclosure.

Referring now to FIG. 3I, a variation from the sensing and ablation system illustrated in FIGS. 3A-3H at reference numbers 220A-220H is now illustrated at reference number 220I. The sensing and ablation system 220I shown in FIG. 3I may be the same as the sensing and ablation system 220A-220H illustrated in FIGS. 3A-3H, except that the first electrode 226I is the needle portion 230 itself, the second electrode 228I is disposed on the side 229 of the probe 222, and the third electrode 234I is disposed on the distal end 224 of the probe 222.

Figure 3J:
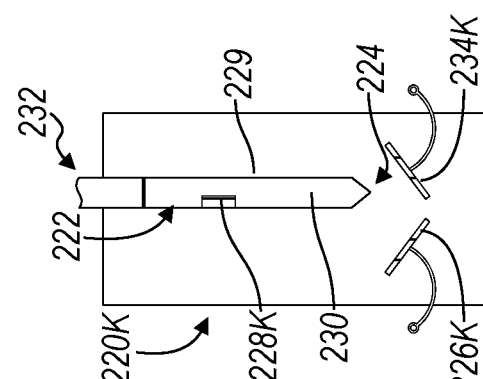
FIG. 3J is a side view of still another sensing and ablation system having a single probe in the form of a monopolar ablation needle, in accordance with the principles of the present disclosure.

Referring now to FIG. 3J, a variation from the sensing and ablation system illustrated in FIGS. 3A-3I at reference numbers 220A-220I is now illustrated at reference number 220J. The sensing and ablation system 220J shown in FIG. 3J may be the same as the sensing and ablation system 220A-220I illustrated in FIGS. 3A-3I, except that the first electrode 226J is disposed at the distal end 224 of the probe 222, the second electrode 228J is disposed on the side 229 of the probe 222, and the third electrode 234J is a patch electrode that is disposed a distance away from the probe 222.

Figure 3K:
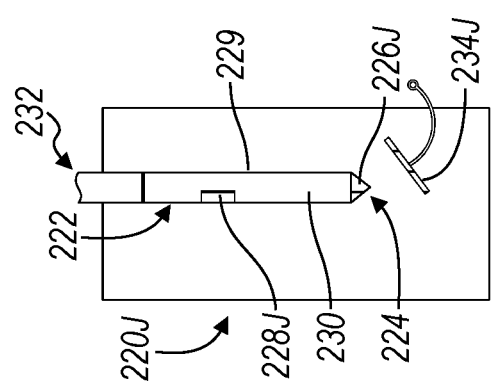
FIG. 3K is a side view of still another sensing and ablation system having a single probe in the form of a monopolar ablation needle, in accordance with the principles of the present disclosure.

Referring now to FIG. 3K, a variation from the sensing and ablation system illustrated in FIGS. 3A-3J at reference numbers 220A-220J is now illustrated at reference number 220K. The sensing and ablation system 220K shown in FIG. 3K may be the same as the sensing and ablation system 220A-220J illustrated in FIGS. 3A-3J, except that the first electrode 226K is a patch electrode disposed a distance away from the probe 222, the second electrode 228K is disposed on the side 229 of the probe 222, and the third electrode 234K is a patch electrode that is disposed a distance away from the probe 222.

Figure 3L:
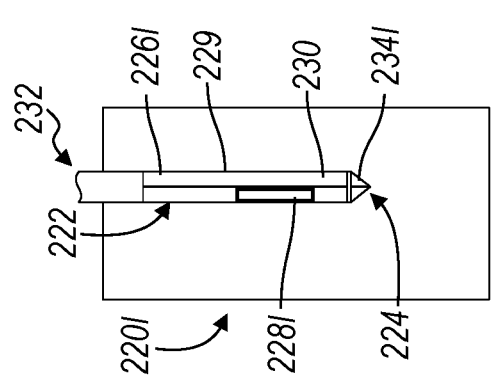
FIG. 3L is a side view of still another sensing and ablation system having a single probe in the form of a monopolar ablation needle, in accordance with the principles of the present disclosure.

Referring now to FIG. 3L, a variation from the sensing and ablation system illustrated in FIGS. 3A-3K at reference numbers 220A-220K is now illustrated at reference number 220L. The sensing and ablation system 220L shown in FIG. 3L may be the same as the sensing and ablation system 220A-220K illustrated in FIGS. 3A-3K, except that the first electrode 226L is disposed proximally of the needle portion 230 of the probe 222, or closer to the proximal end 232 than the needle portion 230 is to the proximal end 232, the second electrode 228L is the needle portion 230 itself, and the third electrode 234L is disposed at the distal end 224 of the probe 222.

Figure 3M:
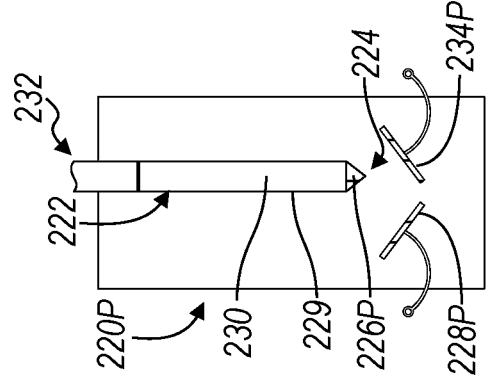
FIG. 3M is a side view of still another sensing and ablation system having a single probe in the form of a monopolar ablation needle, in accordance with the principles of the present disclosure.

Referring now to FIG. 3M, a variation from the sensing and ablation system illustrated in FIGS. 3A-3L at reference numbers 220A-220L is now illustrated at reference number 220M. The sensing and ablation system 220M shown in FIG. 3M may be the same as the sensing and ablation system 220A-220L illustrated in FIGS. 3A-3L, except that the first electrode 226M is disposed proximally of the needle portion 230 of the probe 222, or closer to the proximal 232 than the needle portion 230 is to the proximal end 232, the second electrode 228M is disposed at the distal end 224 of the probe 222, and the third electrode 234M is a patch electrode that is disposed a distance away from the probe 222.

Figure 3N:
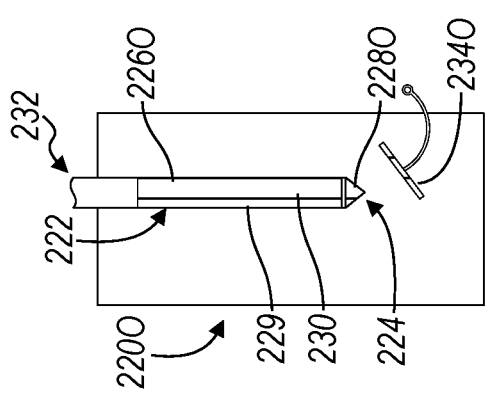
FIG. 3N is a side view of still another sensing and ablation system having a single probe in the form of a monopolar ablation needle, in accordance with the principles of the present disclosure.

Referring now to FIG. 3N, a variation from the sensing and ablation system illustrated in FIGS. 3A-3M at reference numbers 220A-220M is now illustrated at reference number 220N. The sensing and ablation system 220N shown in FIG. 3N may be the same as the sensing and ablation system 220A-220M illustrated in FIGS. 3A-3M, except that the first electrode 226N is disposed proximally of the needle portion 230, or closer to the proximal end 232 than the needle portion 230 is to the proximal end 232, and the second and third electrodes 228N, 234N are patch electrodes that are disposed a distance away from the probe 222 and from each other.

Figure 3O:
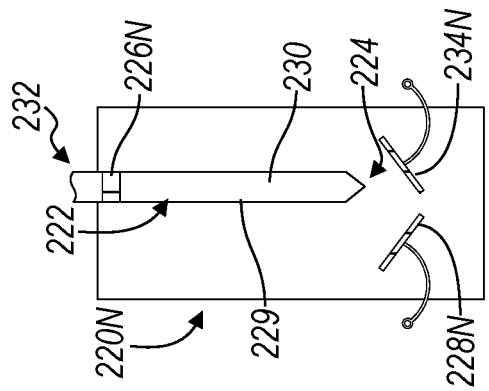
FIG. 3O is a side view of still another sensing and ablation system having a single probe in the form of a monopolar ablation needle, in accordance with the principles of the present disclosure.

Referring now to FIG. 3O, a variation from the sensing and ablation system illustrated in FIGS. 3A-3N at reference numbers 220A-220N is now illustrated at reference number 220O. The sensing and ablation system 220O shown in FIG. 3O may be the same as the sensing and ablation system 220A-220N illustrated in FIGS. 3A-3N, except that the first electrode 226O is the needle portion 230 itself, the second electrode 228O is disposed at the distal end 224 of the probe 220O, and the third electrode 234O is a patch electrode that is disposed a distance away from the probe 222.

Figure 3P:
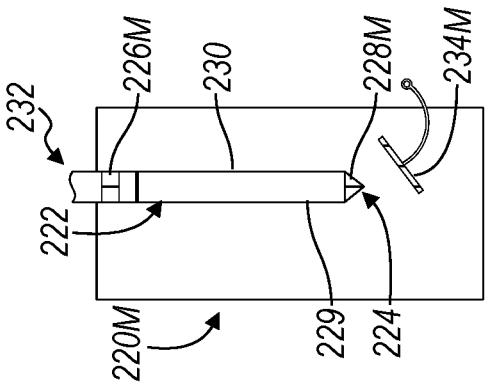
FIG. 3P is a side view of still another sensing and ablation system having a single probe in the form of a monopolar ablation needle, in accordance with the principles of the present disclosure.

Referring now to FIG. 3P, a variation from the sensing and ablation system illustrated in FIGS. 3A-3O at reference numbers 220A-220O is now illustrated at reference number 220P. The sensing and ablation system 220P shown in FIG. 3P may be the same as the sensing and ablation system 220A-220O illustrated in FIGS. 3A-3O, except that the first electrode 226P is disposed at the distal end 224 of the probe 222, and the second and third electrodes 228P, 234P are patch electrodes that are disposed a distance away from the probe 222 and from each other.

Referring now to FIG. 3Q, a variation from the sensing and ablation system illustrated in FIGS. 3A-3P at reference numbers 220A-220P is now illustrated at reference number 220Q. The sensing and ablation system 220Q shown in FIG. 3Q may be the same as the sensing and ablation system 220A-220P illustrated in FIGS. 3A-3P, except that the first electrode 226Q is the needle portion 230 itself, and the second and third electrodes 228Q, 234Q are patch electrodes that are disposed a distance away from the probe 222 and from each other.

Referring now to FIG. 3R, a variation from the sensing and ablation system illustrated in FIGS. 3A-3Q at reference numbers 220A-220Q is now illustrated at reference number 220R. The sensing and ablation system 220R shown in FIG. 3R may be the same as the sensing and ablation system 220A-220Q illustrated in FIGS. 3A-3Q, except that all three electrodes 226R, 228R, 234R are patch electrodes that are disposed a distance away from the probe 222 and from each other. None of the electrodes 226R, 228R, 234R is coupled with the probe 222.

In yet another variation of a sensing and ablation system within the present disclosure is system involving more than one probe. For example, FIGS. 4A-4J illustrate several embodiments of a sensing and ablation system 320A-320J having multiples needles. In FIG. 4A, a sensing and ablation system is illustrated in FIG. 4A and generally indicated reference number 320A. In this variation, a first electrode 326A is located on a first probe 322, and a second electrode 328A is located on a second probe 336. The first and the second probes 322, 336 are in the form of needles having pointed distal ends 324, wherein the probes 322, 336 themselves are ablation electrodes, as described above. Like the probes 22, 122, 222 hereinbefore described, the probes 322, 336 of FIG. 4A are configured to be inserted into the patient's anatomy for ablation of bodily tissue in the patient's anatomy. The first and second electrodes 326A, 328A are each disposed at the distal ends 324 of the probes 322, 336.

The first electrode 326A and the second electrode 328A make up a sensing circuit. One of the first and second electrodes 326A, 328A is an active electrode that is coupled with and energized by an electrode energy source. The other of the first and second electrodes 326A, 328A is a measurement return electrode, which is a neutral electrode that is not configured to be energized by an energy source. (In some variations, an active electrode may also serve as the return electrode). The measurement return electrode is configured to provide data based on the measurement signal, for determining a complex impedance in the patient's anatomy while the active electrode is energized, as explained above. Thus, the measurement signal is passed between the first and second electrodes 326A, 328A.

The sensing and ablation system 320A also includes an ablation circuit, made up of at least one of the probes 322, 336 themselves as the electrode, or one of the first electrode 326A and the second electrode 328A. The ablation circuit is configured to deliver a source ablation signal from at least one of the probes 322, 336 or the first and second electrodes 326A, 328A, which is the ablation active electrode. The ablation active electrode is configured to deliver the source ablation signal to the patient's tissue, and the source ablation signal is configured to travel through the tissue and become an ablation return signal. The ablation circuit is configured to receive the ablation return signal through the ablation return electrode, which may be one of the probes 322, 336, one of the first and second electrodes 326A, 328A, or a skin patch electrode (not shown in FIG. 4A). Thus, the ablation return electrode receives the ablation return signal as the tissue is ablated by the ablation circuit.

Referring now to FIG. 4B, a variation from the sensing and ablation system illustrated in FIG. 4A at reference number 320A is now illustrated at reference number 320B. The sensing and ablation system 320B shown in FIG. 4B may be the same as the sensing and ablation system 320A illustrated in FIG. 4A, except that the second electrode 328B is illustrated behind the needle portion 330 of the probe 322. In other words, the second electrode 328B is located proximally of the needle portion 330, or closer to a proximal end 332 of the probe 322 than the needle portion 330 is to the proximal end 332.

Referring now to FIG. 4C, a variation from the sensing and ablation system illustrated in FIGS. 4A and 4B at reference numbers 320A and 320B is now illustrated at reference number 320C. The sensing and ablation system 320C shown in FIG. 4C may be the same as the sensing and ablation system 320A or 320B illustrated in FIG. 4A or 4B, except that the second electrode 328C is the needle portion 330 itself of the second probe 336.

Referring now to FIG. 4D, a variation from the sensing and ablation system illustrated in FIGS. 4A, 4B, and 4C at reference numbers 320A, 320B, and 320C is now illustrated at reference number 320D. The sensing and ablation system 320D shown in FIG. 4D may be the same as the sensing and ablation system 320A, 320B, or 320C illustrated in FIG. 4A, 4B, or 4C, except that both the first and second electrodes 326D, 328D are illustrated as the needle portions 330 of the probes 322, 336 themselves. In other words, the first electrode 326D is the needle portion 330 of the first probe 322, and the second electrode 328D is the needle portion 330 of the second probe 336.

Referring now to FIG. 4E, a variation from the sensing and ablation system illustrated in FIGS. 4A-4D at reference numbers 320A-320D is now illustrated at reference number 320E. The sensing and ablation system 320E shown in FIG. 4E may be the same as the sensing and ablation system 320A-320D illustrated in FIGS. 4A-4D, except that the first electrode 326E is disposed on the side 329 of the needle portion 330 of the first probe 322, and the second electrode 328E is disposed on the side 329 of the needle portion 320 of the second probe 336.

Referring now to FIG. 4F, a variation from the sensing and ablation system illustrated in FIGS. 4A-4E at reference numbers 320A-320E is now illustrated at reference number 320F. The sensing and ablation system 320F shown in FIG. 4F may be the same as the sensing and ablation system 320A-320E illustrated in FIGS. 4A-4E, except that the first electrode 326F is disposed on the side 329 of the needle portion 330 of the first probe 322, while the second electrode 328F is a skin patch electrode disposed a distance away from the first and second probes 322, 336.

Referring now to FIG. 4G, a variation from the sensing and ablation system illustrated in FIGS. 4A-4F at reference numbers 320A-320F is now illustrated at reference number 320G. The sensing and ablation system 320G shown in FIG. 4G may be the same as the sensing and ablation system 320A-320F illustrated in FIGS. 4A-4F, except that both the first and second electrodes 326G, 328G are skin patch electrodes that are disposed a distance away from the first and second probes 322, 336 and each other.

Referring now to FIG. 4H, a variation from the sensing and ablation system illustrated in FIGS. 4A-4G at reference numbers 320A-320G is now illustrated at reference number 320H. The sensing and ablation system 320H shown in FIG. 4H may be the same as the sensing and ablation system 320A-320G illustrated in FIGS. 4A-4G, except that both the first and second electrodes 326H, 328H are coupled with the first probe 322. The first electrode 326H is disposed proximally of the needle portion 330, such that the first electrode 326H is disposed closer to the proximal end 332 of the first probe 322 than the needle portion 330 is to the proximal end 332. The second electrode 328H is attached to the distal end 324 of the first probe 322.

Referring now to FIG. 4I, a variation from the sensing and ablation system illustrated in FIGS. 4A-4H at reference numbers 320A-320H is now illustrated at reference number 320I. The sensing and ablation system 320I shown in FIG. 4I may be the same as the sensing and ablation system 320A-320H illustrated in FIGS. 4A-4H, except that both the first and second electrodes 326I, 328I are coupled with the first probe 322, wherein the first electrode 326I is the needle portion 330 itself and the second electrode 328I is attached to the distal end 324 of the first probe 322.

Referring now to FIG. 4J, a variation from the sensing and ablation system illustrated in FIGS. 4A-4I at reference numbers 320A-320I is now illustrated at reference number 320J. The sensing and ablation system 320J shown in FIG. 4J may be the same as the sensing and ablation system 320A-320I illustrated in FIGS. 4A-4I, except that the first electrode 326J is the needle portion 330 itself of the first probe 322, and the second electrode 328J is disposed proximally of the needle portion 330 of the second probe 336, such that the second electrode 326J is disposed closer to the proximal end 332 of the second probe 336 than the needle portion 330 is to the proximal end 322.

Further variations of a two-probe system having first and second electrodes are illustrated in FIG. 5.

Referring now to FIG. 6A, a sensing and ablation system comprising four electrodes is illustrated and generally designated at 420A. In the embodiment of FIG. 6A, a pair of ablation potential electrodes 438A, 440A are disposed on a probe 422, which is in the form of a needle having a pointed distal end 424. Accordingly, the probe 422 is a bipolar ablation device. A non-energized portion 442 separates the pair of ablation potential electrodes 438A, 440A. Like the probes 22, 122, 222, 322 of FIGS. 1A-4J, the probe 422 of FIG. 6A is configured to be inserted into the patient's anatomy for ablation of bodily tissue in the patient's anatomy.

The pair of ablation electrodes 438A, 440A forms an ablation circuit. The first ablation electrode 438A of the pair of ablation electrodes 438A, 440A delivers a source ablation signal, which travels through tissue near the probe 422 and turns into an ablation return signal, which is received by the second ablation electrode 440A. Likewise, the second ablation electrode 440A delivers a source ablation signal, which travels through tissue near the probe 422 and turns into an ablation return signal, which is received by the first ablation electrode 438A. Thus, each of the ablation electrodes 438A, 440A sends an ablation signal into the patient's tissue to ablate the tissue. In the alternative, a single one of the pair of ablation electrodes 438A, 440A may send the ablation signal while the other of the pair of ablation electrodes 438A, 440A receives the ablation return signal. Another electrode may also serve as the return electrode.

A first skin patch electrode 444A and a second skin patch electrode 446A make up a sensing circuit. One or both of the patch electrodes 444A, 446A sends out a sensing signal that is received by the other of the patch electrodes 444A, 446A. Thus, at least one of the patch electrodes 444A, 446A is an active electrode that is coupled with and energized by an electrode energy source. The receiving patch electrode(s) 444A, 446A is configured to provide data based on the measurement signal, for determining a complex impedance in the patient's anatomy while the active electrode is energized, as explained above. Thus, the measurement signal is passed between the patch electrodes 444A, 446A.

With the variation of FIG. 6A, the measurement source electrode and the ablation source electrode and the measurement return electrode and ablation return electrode may be different electrodes or the same electrodes. For example, although the pair of electrodes 438A, 440A is described as forming the ablation circuit and the pair of electrodes 444A, 446A is described as forming the measurement circuit, any of the electrodes 438A, 440A, 444A, 446A may form a part of the ablation circuit and/or the measurement circuit, if desired. In FIG. 6A, each of the electrodes 438A, 440A used in the ablation circuit are coupled with the probe 422, while each of the electrodes 444A, 446A used in the sensing circuit are skin patch electrodes that are disposed a distance away from the probe 422.

Referring now to FIG. 6B, a variation from the sensing and ablation system illustrated in FIG. 6A at reference number 420A is now illustrated at reference number 420B. The sensing and ablation system 420B shown in FIG. 6B may be the same as the sensing and ablation system 420A illustrated in FIG. 6A, except that only one of the sensing circuit electrodes is a patch electrode 446B, while the other electrode 444B making up the sensing circuit is disposed on the side 429 of the needle portion 430 of the probe 422 on the first ablation electrode 438B. The first and second ablation electrodes 438B, 440B remain on the probe 422 as shown in FIG. 6A.

Referring now to FIG. 6C, a variation from the sensing and ablation system illustrated in FIGS. 6A and 6B at reference numbers 420A and 420B is now illustrated at reference number 420C. The sensing and ablation system 420C shown in FIG. 6C may be the same as the sensing and ablation system 420A or 420B illustrated in FIG. 6A or 6B, except that the first sensing electrode 444C is disposed on the side 429 of the needle portion 430 of the probe 422 on the second ablation electrode 440C, where the second ablation electrode 440C extends to the distal end 424 of the needle portion 430. The second sensing electrode 446C is a patch electrode as previously shown in FIGS. 6A and 6B, and the first and second ablation electrodes 438C, 440C remain on the probe 422 as shown in FIGS. 6A and 6B.

Referring now to FIG. 6D, a variation from the sensing and ablation system illustrated in FIGS. 6A, 6B, and 6C at reference numbers 420A, 420B, and 420C is now illustrated at reference number 420D. The sensing and ablation system 420D shown in FIG. 6D may be the same as the sensing and ablation system 420A, 420B, or 420C illustrated in FIG. 6A, 6B, or 6C, except that the first ablation electrode 438D is also used as the first sensing electrode 444D in the sensing circuit. The second sensing electrode 446D is a patch electrode as previously shown in FIGS. 6A-6C, and the second ablation electrode 440D remains on the distal end 424 of the probe 422 as shown in FIGS. 6A-6C.

Referring now to FIG. 6E, a variation from the sensing and ablation system illustrated in FIGS. 6A-6D at reference numbers 420A-420D is now illustrated at reference number 420E. The sensing and ablation system 420E shown in FIG. 6E may be the same as the sensing and ablation system 420A-420D illustrated in FIGS. 6A-6D, except that the second ablation electrode 440E disposed at the distal end 424 is also used as the first sensing electrode 444E in the sensing circuit. The second sensing electrode 446E is a patch electrode as previously shown in FIGS. 6A-6D, and the first ablation electrode 440E remains on the probe 422 as shown in FIGS. 6A-6D.

Referring now to FIG. 6F, a variation from the sensing and ablation system illustrated in FIGS. 6A-6E at reference numbers 420A-420E is now illustrated at reference number 420F. The sensing and ablation system 420F shown in FIG. 6F may be the same as the sensing and ablation system 420A-420E illustrated in FIGS. 6A-6E, except that the first sensing electrode 444F is disposed on the probe 422 in the area 442 between the first and second ablation electrodes 438F, 440F, which are disposed on the probe 422 as illustrated in FIGS. 6A-6E. The second sensing electrode 446F is a patch electrode as previously shown in FIGS. 6A-6E, which is spaced a distance away from the probe 422.

Referring now to FIG. 6G, a variation from the sensing and ablation system illustrated in FIGS. 6A-6F at reference numbers 420A-420F is now illustrated at reference number 420G. The sensing and ablation system 420G shown in FIG. 6G may be the same as the sensing and ablation system 420A-420F illustrated in FIGS. 6A-6F, except that the first sensing electrode 444G is disposed on the distal tip 424 of the probe 422, distally of the second ablation electrode 440G, or farther from the proximal end 432 of the probe 422 than the ablation electrodes 438G, 440G are from the proximal end 432 of the probe 422. The second sensing electrode 446G is a patch electrode as previously shown in FIGS. 6A-6F, which is spaced a distance away from the probe 422. The first and second ablation electrodes 438G, 440G remain on the probe 422 as shown in FIGS. 6A-6F.

Referring now to FIG. 6H, a variation from the sensing and ablation system illustrated in FIGS. 6A-6G at reference numbers 420A-420G is now illustrated at reference number 420H. The sensing and ablation system 420H shown in FIG. 6H may be the same as the sensing and ablation system 420A-420G illustrated in FIGS. 6A-6G, except that the first sensing electrode 444H is disposed at the proximal end 432 of the probe 422, farther from the distal end 424 than the first and second ablation electrodes 438H, 440H are from the distal end 424. The second sensing electrode 446H is a patch electrode as previously shown in FIGS. 6A-6G, which is spaced a distance away from the probe 422. The first and second ablation electrodes 438H, 440H remain on the probe 422 as shown in FIGS. 6A-6G.

Figure 6I:
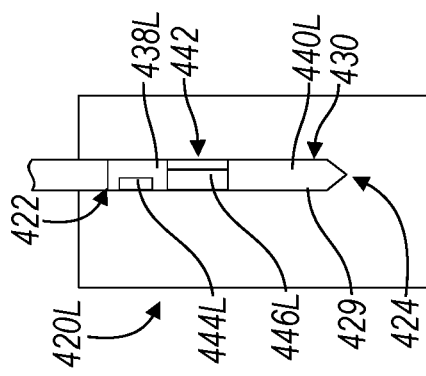
FIG. 6I is a side view of still another sensing and ablation system having a single probe in the form of a bipolar ablation needle, in accordance with the principles of the present disclosure.

Referring now to FIG. 6I, a variation from the sensing and ablation system illustrated in FIGS. 6A-6H at reference numbers 420A-420H is now illustrated at reference number 420I. The sensing and ablation system 420I shown in FIG. 6I may be the same as the sensing and ablation system 420A-420H illustrated in FIGS. 6A-6H, except that the first sensing electrode 444I is disposed on the side 429 of the needle portion 430 of the probe 422 on the first ablation electrode 438I and the second sensing electrode 446I is disposed on the side 429 of the needle portion 430 of the probe 422 on the second ablation electrode 440I. In another variation (not pictured), both first and second sensing electrodes 444I, 446I may be located on the same ablation electrode 438I, 440I. The first and second ablation electrodes 438I, 440I remain on the probe 422 as shown in FIGS. 6A-6H.

Figure 6J:
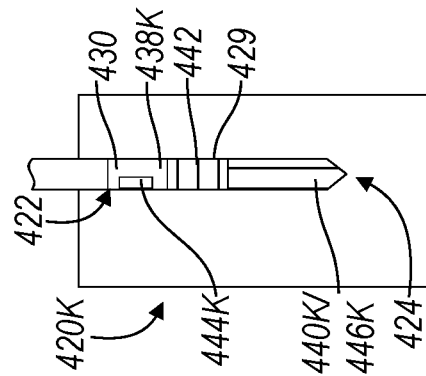
FIG. 6J is a side view of still another sensing and ablation system having a single probe in the form of a bipolar ablation needle, in accordance with the principles of the present disclosure.

Referring now to FIG. 6J, a variation from the sensing and ablation system illustrated in FIGS. 6A-6I at reference numbers 420A-420I is now illustrated at reference number 420J. The sensing and ablation system 420J shown in FIG. 6J may be the same as the sensing and ablation system 420A-420I illustrated in FIGS. 6A-6I, except that the first sensing electrode 444J is disposed on the side 429 of the needle portion 430 of the probe 422 on the first ablation electrode 438J and the first ablation electrode 438J is used as the second sensing electrode 446J. The first and second ablation electrodes 438J, 440J remain on the probe 422 as shown in FIGS. 6A-6I.

Figure 6K:
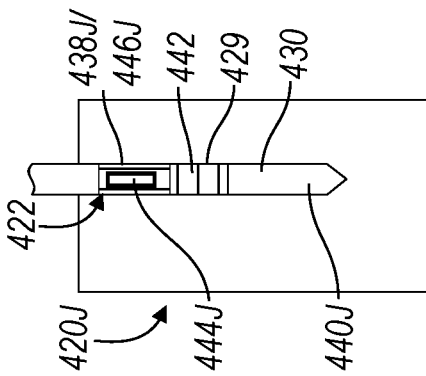
FIG. 6K is a side view of still another sensing and ablation system having a single probe in the form of a bipolar ablation needle, in accordance with the principles of the present disclosure.

Referring now to FIG. 6K, a variation from the sensing and ablation system illustrated in FIGS. 6A-6J at reference numbers 420A-420J is now illustrated at reference number 420K. The sensing and ablation system 420K shown in FIG. 6K may be the same as the sensing and ablation system 420A-420J illustrated in FIGS. 6A-6J, except that the first sensing electrode 444K is disposed on the side 429 of the needle portion 430 of the probe 422 on the first ablation electrode 438K and the second ablation electrode 440K is used as the second sensing electrode 446K. The first and second ablation electrodes 438K, 440K remain on the probe 422 as shown in FIGS. 6A-6J.

Figure 6L:
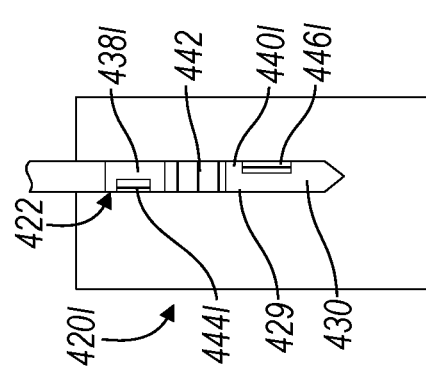
FIG. 6L is a side view of still another sensing and ablation system having a single probe in the form of a bipolar ablation needle, in accordance with the principles of the present disclosure.

Referring now to FIG. 6L, a variation from the sensing and ablation system illustrated in FIGS. 6A-6K at reference numbers 420A-420K is now illustrated at reference number 420L. The sensing and ablation system 420L shown in FIG. 6L may be the same as the sensing and ablation system 420A-420K illustrated in FIGS. 6A-6K, except that the first sensing electrode 444L is disposed on the side 429 of the needle portion 430 of the probe 422 on the first ablation electrode 438L and the second ablation electrode 440L is disposed in the area 442 between the first and second ablation electrodes 438L, 440L. The first and second ablation electrodes 438L, 440L remain on the probe 422 as shown in FIGS. 6A-6K.

Figure 6M:
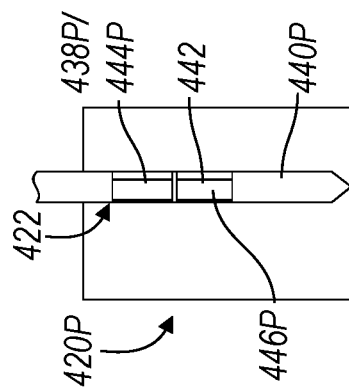
FIG. 6M is a side view of still another sensing and ablation system having a single probe in the form of a bipolar ablation needle, in accordance with the principles of the present disclosure.

Referring now to FIG. 6M, a variation from the sensing and ablation system illustrated in FIGS. 6A-6L at reference numbers 420A-420L is now illustrated at reference number 420M. The sensing and ablation system 420M shown in FIG. 6M may be the same as the sensing and ablation system 420A-420L illustrated in FIGS. 6A-6L, except that the first sensing electrode 444M is disposed on the side 429 of the needle portion 430 of the probe 422 on the first ablation electrode 438M, and the second sensing electrode 446M is disposed on the distal tip 424 of the probe 422, distally of the second ablation electrode 440M, or farther from the proximal end 432 of the probe 422 than the ablation electrodes 438M, 440M are from the proximal end 432 of the probe 422. The first and second ablation electrodes 438M, 440M remain on the probe 422 as shown in FIGS. 6A-6L.

Figure 6N:
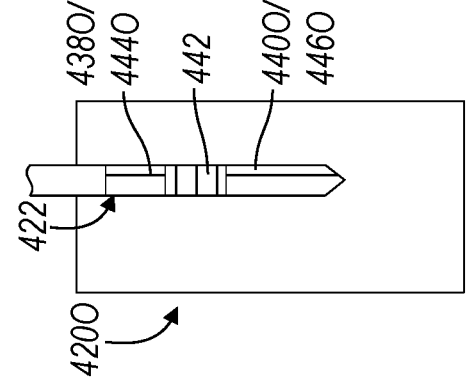
FIG. 6N is a side view of still another sensing and ablation system having a single probe in the form of a bipolar ablation needle, in accordance with the principles of the present disclosure.

Referring now to FIG. 6N, a variation from the sensing and ablation system illustrated in FIGS. 6A-6M at reference numbers 420A-420M is now illustrated at reference number 420N. The sensing and ablation system 420N shown in FIG. 6N may be the same as the sensing and ablation system 420A-420M illustrated in FIGS. 6A-6M, except that the first sensing electrode 444N is disposed proximally of the first and second ablation electrodes 438N, 440N, or closer to the proximal end 432 of the probe 422 than the first and second ablation electrodes 438N, 440N are to the proximal end 432. The second sensing electrode 446N is disposed on the side 429 of the needle portion 430 of the probe 422 on the second ablation electrode 440N. The first and second ablation electrodes 438N, 440N remain on the probe 422 as shown in FIGS. 6A-6M.

Figure 6O:
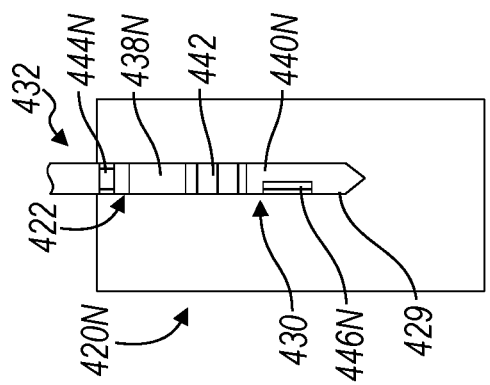
FIG. 6O is a side view of still another sensing and ablation system having a single probe in the form of a bipolar ablation needle, in accordance with the principles of the present disclosure.

Referring now to FIG. 6O, a variation from the sensing and ablation system illustrated in FIGS. 6A-6N at reference numbers 420A-420N is now illustrated at reference number 420O. The sensing and ablation system 420O shown in FIG. 6O may be the same as the sensing and ablation system 420A-420N illustrated in FIGS. 6A-6N, except that the first ablation electrode 438O is used as the first sensing electrode 444O, and the second ablation electrode 440O is used as the second sensing electrode 446O. The first and second ablation electrodes 438O, 440O remain on the probe 422 as shown in FIGS. 6A-6N.

Figure 6P:
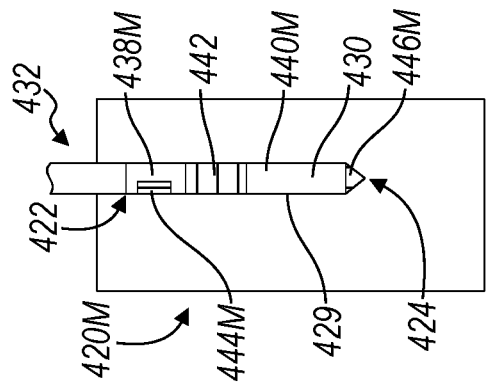
FIG. 6P is a side view of still another sensing and ablation system having a single probe in the form of a bipolar ablation needle, in accordance with the principles of the present disclosure.

Referring now to FIG. 6P, a variation from the sensing and ablation system illustrated in FIGS. 6A-6O at reference numbers 420A-420O is now illustrated at reference number 420P. The sensing and ablation system 420P shown in FIG. 6P may be the same as the sensing and ablation system 420A-420O illustrated in FIGS. 6A-6O, except that the first ablation electrode 438P is used as the sensing electrode 444P, and the second sensing electrode 446P is disposed in the area 442 between the first and second ablation electrodes 438P, 440P. The first and second ablation electrodes 438P, 440P remain on the probe 422 as shown in FIGS. 6A-6O.

Referring now to FIG. 6Q, a variation from the sensing and ablation system illustrated in FIGS. 6A-6P at reference numbers 420A-420P is now illustrated at reference number 420Q. The sensing and ablation system 420Q shown in FIG. 6Q may be the same as the sensing and ablation system 420A-420P illustrated in FIGS. 6A-6P, except that the first ablation electrode 438Q is used as the first sensing electrode 444Q, and the second sensing electrode 446Q is disposed on the distal tip 424 of the probe 422, distally of the second ablation electrode 440Q, or farther from the proximal end 432 of the probe 422 than the ablation electrodes 438Q, 440Q are from the proximal end 432 of the probe 422. The first and second ablation electrodes 438Q, 440Q remain on the probe 422 as shown in FIGS. 6A-6P.

Referring now to FIG. 6R, a variation from the sensing and ablation system illustrated in FIGS. 6A-6Q at reference numbers 420A-420Q is now illustrated at reference number 420R. The sensing and ablation system 420R shown in FIG. 6R may be the same as the sensing and ablation system 420A-420Q illustrated in FIGS. 6A-6Q, except that the first sensing electrode 444R is disposed proximally of the first and second ablation electrodes 438R, 440R, or closer to the proximal end 432 of the probe 422 than the first and second ablation electrodes 438R, 440R are to the proximal end 432. The second ablation electrode 440R is used as the second sensing electrode 446R. The first and second ablation electrodes 438R, 440R remain on the probe 422 as shown in FIGS. 6A-6Q.

Referring now to FIG. 6S, a variation from the sensing and ablation system illustrated in FIGS. 6A-6R at reference numbers 420A-420R is now illustrated at reference number 420S. The sensing and ablation system 420S shown in FIG. 6S may be the same as the sensing and ablation system 420A-420R illustrated in FIGS. 6A-6R, except that the first sensing electrode 444S is disposed in the area 442 between the first and second ablation electrode 438S, 440S, and the second sensing electrode 446S is disposed on the distal tip 424 of the probe 422, distally of the second ablation electrode 440S, or farther from the proximal end 432 of the probe 422 than the ablation electrodes 438S, 440S are from the proximal end 432 of the probe 422. The first and second ablation electrodes 438S, 440S remain on the probe 422 as shown in FIGS. 6A-6R.

Referring now to FIG. 6T, a variation from the sensing and ablation system illustrated in FIGS. 6A-6S at reference numbers 420A-420S is now illustrated at reference number 420T. The sensing and ablation system 420T shown in FIG. 6T may be the same as the sensing and ablation system 420A-420S illustrated in FIGS. 6A-6S, except that the first sensing electrode 444T is disposed proximally of the first and second ablation electrodes 438T, 440T, or closer to the proximal end 432 of the probe 422 than the first and second ablation electrodes 438T, 440T are to the proximal end 432. The second sensing electrode 446T is disposed in the area 442 between the first and second ablation electrodes 438T, 440T. The first and second ablation electrodes 438T, 440T remain on the probe 422 as shown in FIGS. 6A-6S.

Referring now to FIG. 6U, a variation from the sensing and ablation system illustrated in FIGS. 6A-6T at reference numbers 420A-420T is now illustrated at reference number 420U. The sensing and ablation system 420U shown in FIG. 6U may be the same as the sensing and ablation system 420A-420T illustrated in FIGS. 6A-6T, except that the first sensing electrode 444U is disposed proximally of the first and second ablation electrodes 438U, 440U, or closer to the proximal end 432 of the probe 422 than the first and second ablation electrodes 438U, 440U are to the proximal end 432. The second sensing electrode 446U is disposed at the distal end 424 of the probe 422, further from the proximal end 432 than the ablation electrodes 438U, 440U are from the proximal end 432. The first and second ablation electrodes 438U, 440U remain on the probe 422 as shown in FIGS. 6A-6T.

Referring now to FIG. 7A, a sensing and ablation system comprising five electrodes is illustrated and generally designated at 520A. In the embodiment of FIG. 7A, a pair of ablation potential electrodes 538A, 540A are disposed on a probe 522, which is in the form of a needle having a pointed distal end 524, similar to the variations shown in FIGS. 6A-6U. Accordingly, the probe 522 is a bipolar ablation device. A non-energized portion 542 separates the pair of ablation potential electrodes 538A, 540A. Like the probes 22, 122, 222, 322, 422 of FIGS. 1A-4J and 6A-6U, the probe 522 of FIG. 7A is configured to be inserted into the patient's anatomy for ablation of bodily tissue in the patient's anatomy.

The pair of ablation electrodes 538A, 540A forms an ablation circuit. The first ablation electrode 538A of the pair of ablation electrodes 538A, 540A delivers a source ablation signal, which travels through tissue near the probe 522 and turns into an ablation return signal, which is received by the second ablation electrode 540A. Likewise, the second ablation electrode 540A delivers a source ablation signal, which travels through tissue near the probe 522 and turns into an ablation return signal, which is received by the first ablation electrode 538A. Thus, each of the ablation electrodes 538A, 540A sends an ablation signal into the patient's tissue to ablate the tissue. In the alternative, a single one of the pair of ablation electrodes 538A, 540A may send the ablation signal while the other of the pair of ablation electrodes 538A, 540A receives the ablation return signal.

A first sensing electrode 544A, a second sensing electrode 546A, and a third sensing electrode 550A make up a sensing circuit. One or more of the sensing electrodes 544A, 546A, 550A sends out a sensing signal that is received another of the sensing electrodes 544A, 546A, 550A. Thus, at least one of the sensing electrodes 544A, 546A, 550A is an active electrode that is coupled with and energized by an electrode energy source. The receiving sensing electrode(s) 544A, 546A, 550A is configured to provide data based on the measurement signal, for determining a complex impedance in the patient's anatomy while the active electrode is energized, as explained above. Thus, the measurement signal is passed between two or three of the sensing electrodes 544A, 546A, 550A. As with the embodiment of FIGS. 3A-3R, two of the sensing electrodes 544A, 546A, 550A may be used at a time, but the three can be switched among to allow measurement in more than one location.

With the variation of FIG. 7A, the measurement source electrode and the ablation source electrode and the measurement return electrode and ablation return electrode may be different electrodes or the same electrodes. For example, although the pair of electrodes 538A, 540A are described as forming the ablation circuit and the electrodes 544A, 546A, 550A are described as forming the measurement circuit, any of the electrodes 538A, 540A, 544A, 546A, 550A may form a part of the ablation circuit and/or the measurement circuit, if desired.

In FIG. 7A, each of the electrodes 438A, 440A used in the ablation circuit are coupled with the probe 422. The first sensing electrode 544A is also coupled with the probe 522 and is disposed at the proximal end 532 of the probe 522, farther from the distal end 524 than the first and second ablation electrodes 538A, 540A are from the distal end 524. The second sensing electrode 546A is coupled with the probe 522 and is disposed at the distal end 524 of the probe 522. The third sensing electrode 550A is a skin patch electrode that is disposed a distance away from the probe 522, such as on the surface of a patient's skin.

Referring now to FIG. 7B, a variation from the sensing and ablation system illustrated in FIG. 7A at reference number 520A is now illustrated at reference number 520B. The sensing and ablation system 520B shown in FIG. 7B may be the same as the sensing and ablation system 520A illustrated in FIG. 7A, except that the first and second ablation electrodes 538B, 540B are used as the first and second sensing electrodes 544B, 546B. The third sensing electrode 550B remains as a patch electrode spaced a distance away from the probe 522. The first and second ablation electrodes 538B, 540B remain on the probe 522 as shown in FIG. 7A.

Referring now to FIG. 7C, a variation from the sensing and ablation system illustrated in FIGS. 7A and 7B at reference numbers 520A and 520B is now illustrated at reference number 520C. The sensing and ablation system 520C shown in FIG. 7C may be the same as the sensing and ablation system 520A or 520B illustrated in FIG. 7A or 7B, except that the first sensing electrode 544C is disposed on the side 529 of the needle portion 530 of the probe 522 on the first ablation electrode 538C and the second sensing electrode 546C is disposed on the side 529 of the needle portion 530 of the probe 522 on the second ablation electrode 540C. The third sensing electrode 550C is a patch electrode as previously shown in FIGS. 7A and 7B, and the first and second ablation electrodes 538C, 540C remain on the probe 522 as shown in FIGS. 7A and 7B.

Figure 7D:
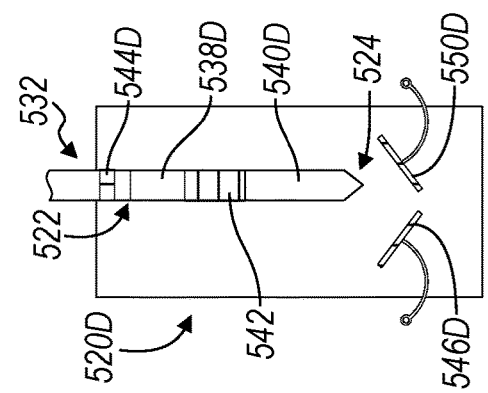
FIG. 7D is a side view of still another sensing and ablation system having a single probe in the form of a bipolar ablation needle, in accordance with the principles of the present disclosure.

Referring now to FIG. 7D, a variation from the sensing and ablation system illustrated in FIGS. 7A-7C at reference numbers 520A-520C is now illustrated at reference number 520D. The sensing and ablation system 520D shown in FIG. 7D may be the same as the sensing and ablation system 520A-520C illustrated in FIGS. 7A-7C, except that the first sensing electrode 544D is disposed at the proximal end 532 of the probe 522, farther from the distal end 524 than the first and second ablation electrodes 538D, 540D are from the distal end 524. The second sensing electrode 546D and the third sensing electrode 550D are patch electrodes that are disposed a distance away from the probe 522 and from each other. The first and second ablation electrodes 538D, 540D remain on the probe 522 as shown in FIGS. 7A-7C.

Figure 7E:
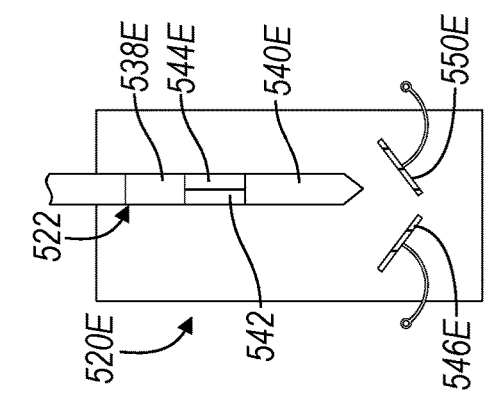
FIG. 7E is a side view of still another sensing and ablation system having a single probe in the form of a bipolar ablation needle, in accordance with the principles of the present disclosure.

Referring now to FIG. 7E, a variation from the sensing and ablation system illustrated in FIGS. 7A-7D at reference numbers 520A-520D is now illustrated at reference number 520E. The sensing and ablation system 520E shown in FIG. 7E may be the same as the sensing and ablation system 520A-520D illustrated in FIGS. 7A-7D, except that the first sensing electrode 544E is disposed in the area 542 between the first and second ablation electrodes 538E, 540E. The second sensing electrode 546E and the third sensing electrode 550E are patch electrodes that are disposed a distance away from the probe 522 and from each other. The first and second ablation electrodes 538E, 540E remain on the probe 522 as shown in FIGS. 7A-7D.

Figure 7F:
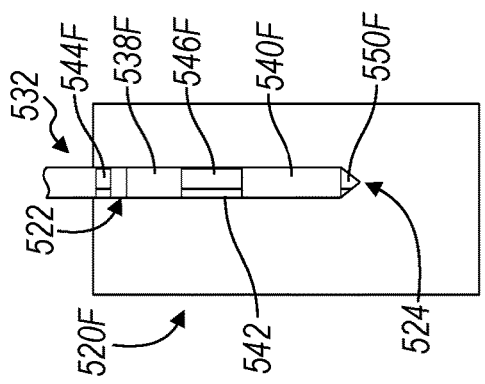
FIG. 7F is a side view of still another sensing and ablation system having a single probe in the form of a bipolar ablation needle, in accordance with the principles of the present disclosure.

Referring now to FIG. 7F, a variation from the sensing and ablation system illustrated in FIGS. 7A-7E at reference numbers 520A-520E is now illustrated at reference number 520F. The sensing and ablation system 520F shown in FIG. 7F may be the same as the sensing and ablation system 520A-520E illustrated in FIGS. 7A-7E, except that the first sensing electrode 544F is disposed on the probe 522 at the proximal end 532 of the probe 522, farther from the distal end 524 than the first and second ablation electrodes 538F, 540F are from the distal end 524. The second sensing electrode 546F is disposed on the probe 522 in the area 542 between the first and second ablation electrodes 538F, 540F, which are disposed on the probe 522 as illustrated in FIGS. 7A-7E. The third sensing electrode 550F is disposed at the distal end 524 of the probe 522.

Figure 7G:
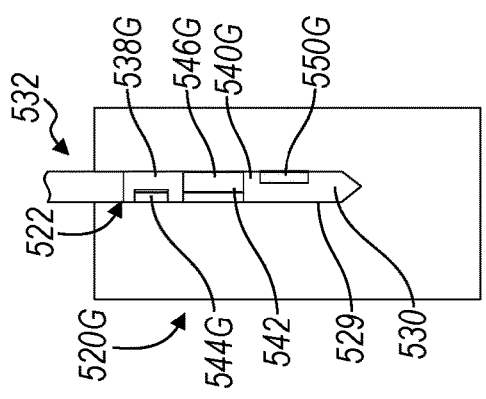
FIG. 7G is a side view of still another sensing and ablation system having a single probe in the form of a bipolar ablation needle, in accordance with the principles of the present disclosure.

Referring now to FIG. 7G, a variation from the sensing and ablation system illustrated in FIGS. 7A-7F at reference numbers 520A-520F is now illustrated at reference number 520G. The sensing and ablation system 520G shown in FIG. 7G may be the same as the sensing and ablation system 520A-520F illustrated in FIGS. 7A-7F, except that the first sensing electrode 544G is disposed on the side 529 of the needle portion 530 of the probe 522 on the first ablation electrode 538G, the second sensing electrode 546G is disposed on the area 542 between the first and second ablation electrodes 538G, 540G, and the third sensing electrode 550G is disposed on the side 529 of the needle portion 530 of the probe 522 on the second ablation electrode 540G. The first and second ablation electrodes 538G, 540G remain on the probe 522 as shown in FIGS. 7A-7F.

Figure 7H:
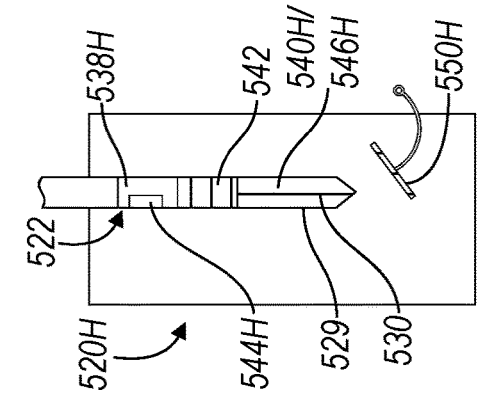
FIG. 7H is a side view of still another sensing and ablation system having a single probe in the form of a bipolar ablation needle, in accordance with the principles of the present disclosure.

Referring now to FIG. 7H, a variation from the sensing and ablation system illustrated in FIGS. 7A-7G at reference numbers 520A-520G is now illustrated at reference number 520H. The sensing and ablation system 520H shown in FIG. 7H may be the same as the sensing and ablation system 520A-520G illustrated in FIGS. 7A-7G, except that the first sensing electrode 544H is disposed on the side 529 of the needle portion 530 of the probe 522 on the first ablation electrode 538H, the second ablation electrode 540H is used as the second sensing electrode 546H, and the third sensing electrode 550H is a patch electrode that is spaced a distance away from the probe 522. The first and second ablation electrodes 538H, 540H remain on the probe 522 as shown in FIGS. 7A-7G.

Figure 7I:
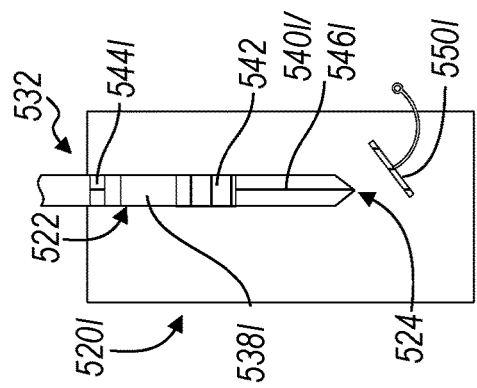
FIG. 7I is a side view of still another sensing and ablation system having a single probe in the form of a bipolar ablation needle, in accordance with the principles of the present disclosure.

Referring now to FIG. 7I, a variation from the sensing and ablation system illustrated in FIGS. 7A-7H at reference numbers 520A-520H is now illustrated at reference number 520I. The sensing and ablation system 520I shown in FIG. 7I may be the same as the sensing and ablation system 520A-520H illustrated in FIGS. 7A-7H, except that the first sensing electrode 544I is disposed on the probe 522 at the proximal end 532 of the probe 522, farther from the distal end 524 than the first and second ablation electrodes 538I, 540I are from the distal end 524. The second ablation electrode 540I is used as the second sensing electrode 546I, and the third sensing electrode 550I is a patch electrode that is spaced a distance away from the probe 522. The first and second ablation electrodes 538I, 540I remain on the probe 522 as shown in FIGS. 7A7H.

Figure 7J:
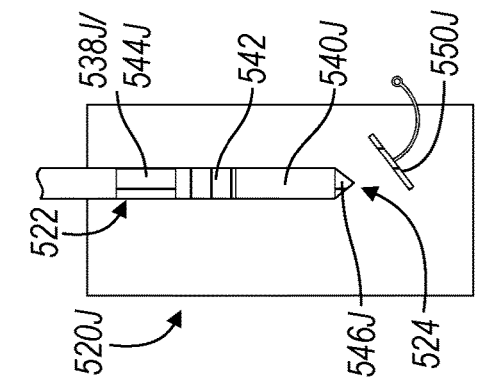
FIG. 7J is a side view of still another sensing and ablation system having a single probe in the form of a bipolar ablation needle, in accordance with the principles of the present disclosure.

Referring now to FIG. 7J, a variation from the sensing and ablation system illustrated in FIGS. 7A-7I at reference numbers 520A-520I is now illustrated at reference number 520J. The sensing and ablation system 520J shown in FIG. 7J may be the same as the sensing and ablation system 520A-520I illustrated in FIGS. 7A-7I, except that the first ablation electrode 538J is used as the first sensing electrode 544J, the second sensing electrode 546J is disposed at the distal end 524 of the probe 522, and the third sensing electrode 550J is a patch electrode that is spaced a distance away from the probe 522. The first and second ablation electrodes 538J, 540J remain on the probe 522 as shown in FIGS. 7A-7I.

Figure 7K:
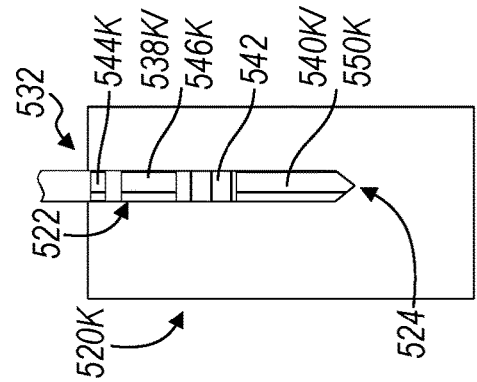
FIG. 7K is a side view of still another sensing and ablation system having a single probe in the form of a bipolar ablation needle, in accordance with the principles of the present disclosure.

Referring now to FIG. 7K, a variation from the sensing and ablation system illustrated in FIGS. 7A-7J at reference numbers 520A-520J is now illustrated at reference number 520K. The sensing and ablation system 520K shown in FIG. 7K may be the same as the sensing and ablation system 520A-520J illustrated in FIGS. 7A-7J, except that the first sensing electrode 544K is disposed proximally of the first and second ablation electrodes 538K, 540K, or closer to the proximal end 532 of the probe 522 than the first and second ablation electrodes 538K, 540K are to the proximal end 532. In addition, the first ablation electrode 538K is used as the second sensing electrode 546K, and the second ablation electrode 540K is used as the third sensing electrode 546K. The first and second ablation electrodes 538K, 540K remain on the probe 522 as shown in FIGS. 7A-7J.

Further variations of a sensing and ablation system having a sensing circuit with three electrodes and an ablation circuit with two electrodes are illustrated in FIGS. 8A and 8B.

These teachings can be expanded further to include instruments that include at least two probes with four or more electrodes. For example, FIGS. 9A-9J illustrate several embodiments of a sensing and ablation system 920A-920J having multiples needles, each having at least two electrodes disposed thereon.

In FIG. 9A, a sensing and ablation system is illustrated in FIG. 9A and generally indicated reference number 620A. In this variation, a pair of ablation potential electrodes 638A, 640A is disposed on a first probe 622, which is in the form of a needle having a pointed distal end 624. Similarly, another pair of ablation potential electrodes 654A, 656A are disposed on a second probe 636 (in the form of a needle having a pointed distal end 658), the second probe 636 being spaced a distance away from the first probe 622. Accordingly, the probes 622, 636 are bipolar ablation devices. Non-energized portions 642, 660 separate the pairs of ablation potential electrodes 638A, 640A, 654A, 656A, respectively. Like the probes 22, 122, 222, 322, 422, 522 of FIGS. 1A-4J and 6A-7K, the probes 622, 636 of FIG. 9A are configured to be inserted into the patient's anatomy for ablation of bodily tissue in the patient's anatomy.

The pairs of ablation electrodes 638A, 640A, 654A, 656A form one or more ablation circuits. For example, one or more of the ablation electrodes 638A, 640A, 654A, 656A delivers a source ablation signal, which travels through tissue near the probes 622, 636 and turns into an ablation return signal, which is received by one of the other ablation electrodes 638A, 640A, 654A, 656A. Thus, at least one of the ablation electrodes 638A, 640A, 654A, 656A sends an ablation signal into the patient's tissue to ablate the tissue.

A first sensing electrode 644A is disposed on the first probe 622, and a second sensing electrode 646A is disposed on the second probe 636, wherein the first and second sensing electrodes 644A, 646A make up a sensing circuit. One or both of the sensing electrodes 644A, 646A sends out a sensing signal, or measurement signal, that is received by the other of the sensing electrodes 644A, 646A. Thus, at least one of the patch electrodes 644A, 646A is an active electrode that is coupled with and energized by an electrode energy source. The receiving sensing electrode(s) 644A, 646A is configured to provide data based on the measurement signal, for determining a complex impedance in the patient's anatomy while the active electrode is energized, as explained above. Thus, the measurement signal is passed between the sensing electrodes 644A, 646A.

With the variation of FIG. 9A, the measurement source electrode and the ablation source electrode and the measurement return electrode and ablation return electrode may be different electrodes or the same electrodes. For example, although the pairs of electrodes 638A, 640A, 654A, 656A are described as forming the ablation circuit and the pair of electrodes 644A, 646A is described as forming the measurement circuit, any of the electrodes 638A, 640A, 654A, 656A, 644A, 646A may form a part of the ablation circuit and/or the measurement circuit, if desired.

In FIG. 9A, all of the electrodes 638A, 640A, 654A, 656A, 644A, 646A are coupled with the probe 622. The first sensing electrode 644A is disposed on the area 642 between the first and second ablation electrodes 638A, 640A. The second sensing electrode 646A is disposed on the area 660 between the third ablation electrode 654A and the fourth ablation electrode 656A.

Referring now to FIG. 9B, a variation from the sensing and ablation system illustrated in FIG. 9A at reference number 620A is now illustrated at reference number 620B. The sensing and ablation system 620B shown in FIG. 9B may be the same as the sensing and ablation system 620A illustrated in FIG. 9A, except that the first sensing electrode 644B is disposed on the distal end 624 of the first probe 622 and the second sensing electrode 646B is disposed on the distal end 658 of the second probe 636. The first and second ablation electrodes 638B, 640B remain on the first probe 622, and the third and fourth ablation electrodes 654B, 656B remain on the second probe 636, as shown in FIG. 9A.

Referring now to FIG. 9C, a variation from the sensing and ablation system illustrated in FIGS. 9A and 9B at reference numbers 620A and 620B is now illustrated at reference number 620C. The sensing and ablation system 620C shown in FIG. 9C may be the same as the sensing and ablation system 620A or 620B illustrated in FIG. 9A or 9B, except that the second ablation electrode 640C is used as the first sensing electrode 644C and the third ablation electrode 654C is used as the second sensing electrode 646C. The first and second ablation electrodes 638C, 640C remain on the first probe 622, and the third and fourth ablation electrodes 654C, 656C remain on the second probe 636, as shown in FIGS. 9A and 9B.

Referring now to FIG. 9D, a variation from the sensing and ablation system illustrated in FIGS. 9A, 9B, and 9C at reference numbers 620A, 620B, and 620C is now illustrated at reference number 620D. The sensing and ablation system 620D shown in FIG. 9D may be the same as the sensing and ablation system 620A, 620B, or 620C illustrated in FIG. 9A, 9B, or 9C, except that both the sensing electrodes 644D, 646D are disposed on the first probe 622. The first ablation electrode 638D is used as the first sensing electrode 644D, and the second ablation electrode 640D is used as the second sensing electrode 646D. The first and second ablation electrodes 638D, 640D remain on the first probe 622, and the third and fourth ablation electrodes 654D, 656D remain on the second probe 636, as shown in FIGS. 9A-9C.

Referring now to FIG. 9E, a variation from the sensing and ablation system illustrated in FIGS. 9A-9D at reference numbers 620A-620D is now illustrated at reference number 620E. The sensing and ablation system 620E shown in FIG. 9E may be the same as the sensing and ablation system 620A-620D illustrated in FIGS. 9A-9D, except that the second ablation electrode 640E is used as the first sensing electrode 644E, and the second sensing electrode 646E is a patch electrode that is spaced a distance away from the probes 622, 636. The first and second ablation electrodes 638E, 640E remain on the first probe 622, and the third and fourth ablation electrodes 654E, 656E remain on the second probe 636, as shown in FIGS. 9A-9D.

Referring now to FIG. 9F, a variation from the sensing and ablation system illustrated in FIGS. 9A-9E at reference numbers 620A-620E is now illustrated at reference number 620F. The sensing and ablation system 620F shown in FIG. 9F may be the same as the sensing and ablation system 620A-620E illustrated in FIGS. 9A-9E, except that the first ablation electrode 638F is used as the first sensing electrode 644F, and the second sensing electrode 646F is a patch electrode disposed a distance away from the first and second probes 622, 636. The first and second ablation electrodes 638F, 640F remain on the first probe 622, and the third and fourth ablation electrodes 654F, 656F remain on the second probe 636, as shown in FIGS. 9A-9E.

Referring now to FIG. 9G, a variation from the sensing and ablation system illustrated in FIGS. 9A-9F at reference numbers 620A-620F is now illustrated at reference number 620G. The sensing and ablation system 620G shown in FIG. 9G may be the same as the sensing and ablation system 620A-620F illustrated in FIGS. 9A-9F, except that the first sensing electrode 644G is disposed at the distal end 624 of the first probe 622, and the second sensing electrode 646G is a patch electrode that is disposed a distance away from the first and second probes 622, 636. The first and second ablation electrodes 638G, 640G remain on the first probe 622, and the third and fourth ablation electrodes 654G, 656G remain on the second probe 636, as shown in FIGS. 9A-9F.

Referring now to FIG. 9H, a variation from the sensing and ablation system illustrated in FIGS. 9A-9G at reference numbers 620A-620G is now illustrated at reference number 620H. The sensing and ablation system 620H shown in FIG. 9H may be the same as the sensing and ablation system 620A-620G illustrated in FIGS. 9A-9G, except that the first sensing electrode 644H is disposed at the distal end 624 of the first probe 622, and the second sensing electrode 646H is disposed proximally of the needle portion 630 of the second probe 636, such that the second sensing electrode 646H is disposed closer to the proximal end 632 of the second probe 636 than the needle portion 630 is to the proximal end 622. In other words, the second sensing electrode 646H is disposed farther from the distal end 624 of the second probe 636 than the third and fourth ablation electrodes 654H, 656H are from the distal end 624. The first and second ablation electrodes 638H, 640H remain on the first probe 622, and the third and fourth ablation electrodes 654H, 656H remain on the second probe 636, as shown in FIGS. 9A-9G.

Referring now to FIG. 9I, a variation from the sensing and ablation system illustrated in FIGS. 9A-9H at reference numbers 620A-620H is now illustrated at reference number 620I. The sensing and ablation system 620I shown in FIG. 9I may be the same as the sensing and ablation system 620A-620H illustrated in FIGS. 9A-9H, except that the first ablation electrode 638I is used as the first sensing electrode 644I, and the third ablation electrode 654I is used as the second sensing electrode 646I. The first and second ablation electrodes 638I, 640I remain on the first probe 622, and the third and fourth ablation electrodes 654I, 656I remain on the second probe 636, as shown in FIGS. 9A-9H.

Referring now to FIG. 9J, a variation from the sensing and ablation system illustrated in FIGS. 9A-9I at reference numbers 620A-620I is now illustrated at reference number 620J. The sensing and ablation system 620J shown in FIG. 9J may be the same as the sensing and ablation system 620A-620I illustrated in FIGS. 9A-9I, except that the first sensing electrode 644J is disposed on the side 629 of the needle portion 630 of the first probe 622 on the second ablation electrode 640J, and the second sensing electrode 646J is disposed on the side 629 of the needle portion 630 of the second probe 636 on the third ablation electrode 654J. The first and second ablation electrodes 638J, 640J remain on the first probe 622, and the third and fourth ablation electrodes 654J, 656J remain on the second probe 636, as shown in FIGS. 9A-9I.

Figures 10B, 10C:
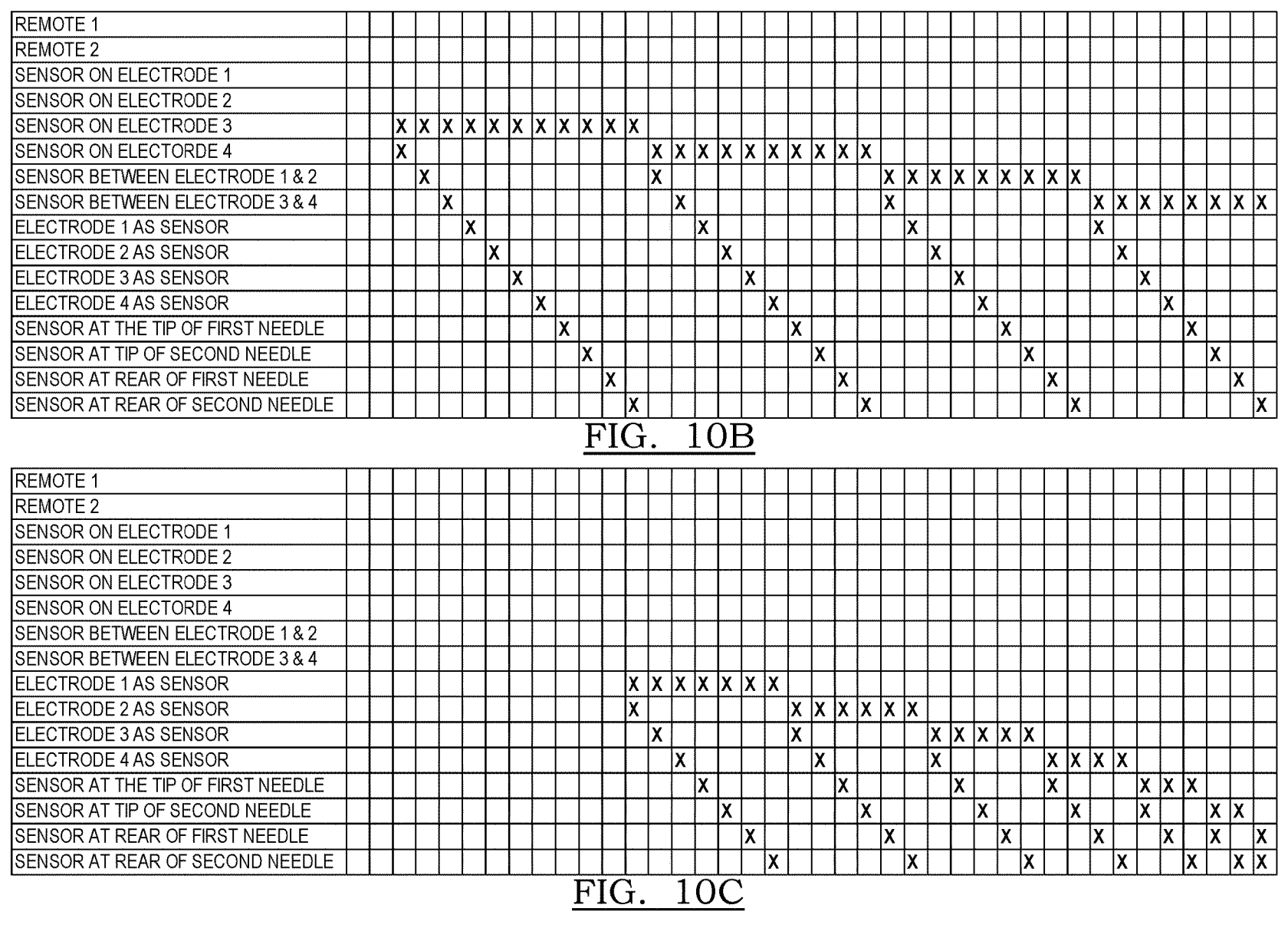

Further variations of a two-probe system having two sets of electrodes on the probe and first and second sensing electrodes are illustrated in FIGS. 10A-10C. Similarly, three or more probes could be used, without falling beyond the spirit and scope of the present disclosure.

A further aspect of the disclosure provides a method of treating a patient using the ablation device as illustrated in a block diagram of FIG. 11. In some embodiments, the method may include using bioelectrical impedance analysis (BIA) for ablation device positioning, power application, and endpoint detection. As used herein, BIA includes passing a low-level current through tissue and while doing so, measuring the resistance and/or the reactance, phase angle shift, and/or capacitance and inductance to determine an impedance. From the reactance and resistance, a complex impedance can be calculated. The complex impedance of tissue (including resistance, scalar impedance, and phase angle) may be analyzed to determine the type or state of tissue.

One of the probes, or needles, described above may be used to create necrotic tissue by introducing energy to a tissue bundle or organ and through application of electro-surgical energy, heating the tissue until the tissue is no longer viable. In some embodiments, the method may include using sensors on an ablation device. The sensors may be able to both emit and receive signals of different types. For example, the method includes emitting at least a low level "measurement level" signal and a high level "ablation level" signal. The measurement signal may be applied at about 50 kHz and 800 µA, by way of example. The ablation signal may be applied at about 400-500 kHz, by way of example.

In some embodiments, the method may include using one of the sensing and ablation systems 20A-D, 120A-G, 220A-R, 320A-J, 420A-U, 520A-K, 620A-J described above, or another apparatus. In some embodiments, the method may include a step 702 of energizing a first electrode with a measurement level of power. The first electrode that is energized may be a skin patch electrode or an electrode that is coupled to a probe, as described above, by way of example. A probe, such as one of the needle probes above may be inserted into a position within a patient's anatomy. The measurement level of power is an amount sufficient to determine or measure a bulk tissue property, such as voltage drop, capacitance, resistance, reactance, or impedance, but preferably not high enough to significantly alter tissue. In other words, applying the measurement level of power to the patient's anatomy allows certain bulk tissue properties to be measured. In one variation, an impedance, such as a complex impedance is determined based on the bulk tissue property or properties measured. Accordingly the method may include a step 704 of measuring a bulk tissue property and/or determining an impedance of the patient's anatomy. A complex impedance includes resistance and reactance.

In some embodiments, the method may further include a step 706 of determining whether the first position of the probe is a desired position of the probe, based on the bulk tissue property and/or the impedance. If the probe is not in a desired position, then probe may then be repositioned. The step 702 of energizing the first electrode with the measurement level of power may then be repeated until it is determined that the probe is in the desired position. The desired position is a position that is desired for ablating tissue in a patient. Based on the impedance determined or the bulk tissue property measured, the operator may estimate whether the probe is in the desired position.

Once the probe is in the desired position, the method may include a step 708 of ablating tissue near the probe by energizing an electrode with an ablation level of power. The ablation level may be provided as high enough to ablate tissue, such as a tumor. The electrodes that are energized with the measurement level of power and the ablation level of power may be the same electrode of different electrodes, such as described with respect to FIGS. 1A-10C. The ablation level of power is higher than the measurement level of power. The ablation level of power may be higher by virtue of higher level of driving current, higher level of driving voltage, same voltage and current but a longer duty cycle, a lower instantaneous driving current or voltage but with an even longer duty cycle.

Thus, the measurement level of power merely causes the electrode to deliver a measurement signal, or a sensing signal, that is directed into the patient's tissue. The sensing signal may be a low level signal that causes no substantial change to the patient's tissue. The sensing signal is sent through the tissue merely to determine the tissue properties so that the operator may know whether the ablation probe has been properly placed to cause tissue ablation. The ablation signal, on the other hand, is high enough to cause tissue necrosis, by way of example. Thus, the sensing signal is lesser, or lower, than the ablation signal.

The impedance may be determined by measuring a property, such as a bulk tissue property, of the patient. The impedance may be determined as a complex impedance, including both resistance (or scalar impedance) and phase angle, by way of example.

In some embodiments, the method may include additional steps and refinements, as described below. For example, the method may include delivering a source measurement signal from the first electrode when the first electrode is energized, the source measurement signal being configured to pass through tissue and become a return measurement signal, the method may further comprise receiving the return measurement signal through a second electrode of the system. The second electrode may be provided on a measurement return device that is spaced a distance away from the probe, such as a skin patch electrode as shown and described above. In the alternative, the second electrode may be coupled with the probe, for example, in any of the configurations shown and described above wherein the second (or first) sensing electrode is disposed on a probe, or where both the first and second sensing electrodes are disposed on a probe.

In some embodiments, the method may include delivering a source ablation signal from an ablation electrode (such as one of the electrodes in one of the systems 20A, 120A, 220A, 320A, 420A, 520A, 620A). Typically, the ablation electrode is provided on a probe, as described above. For example, the method may also include delivering a source ablation signal from an ablation electrode (which could be the first electrode or another electrode) when the ablation electrode is energized, the source ablation signal being configured to pass through tissue and become an ablation return signal, the method may further comprise receiving the ablation return signal through an ablation return electrode of the system. The ablation return electrode may be the first electrode, the second electrode, a third electrode, or another electrode, by way of example. The ablation return electrode may be provided on a return device that is spaced a distance away from the probe, such as a skin patch electrode as shown and described above. In the alternative, the ablation return electrode may be coupled with the probe, for example, in any of the configurations shown and described above.

In one variation, the one or more electrodes serving as the source of the measurement signal and the ablation signal are active electrodes, while the return electrodes are neutral electrodes that are not energized. In another variation, however, both the source electrodes and the return electrodes are energized, such that the measurement source electrode and the measurement return electrode are energized with opposite polarity to each other. Similarly, both the ablation source electrode and the ablation return electrode may be energized with opposite polarity to each other. In another variation, one of the measurement circuit or the ablation circuit may use a neutral return electrode, while the other of the measurement circuit and the ablation circuit has a return electrode that is charged with opposite polarity to the source electrode.

When two electrodes are energized with opposite polarity in the ablation circuit, for example, a first ablation source signal is delivered from a first ablation electrode, and a second source ablation signal is delivered from a second ablation electrode. Each ablation signal turns into a return signal, such that the first ablation return signal is received by the second ablation electrode and the second ablation return signal is received by the first ablation electrode. In such a circuit, electrons flow from each ablation electron in a single direction at a time. As the signals oscillate between each ablation electrode, the electrons race toward whichever electrode has a more positive terminal.

The measurement circuit may operate the same way. The measurement electrodes and the ablation electrodes may be common or different electrodes. For example, when two electrodes are energized with opposite polarity in the measurement circuit, a first measurement source signal is delivered from a first sensing electrode, and a second measurement source signal is delivered from a second sensing electrode. Each measurement signal turns into a return signal, such that the first measurement return signal is received by the second sensing electrode and the second measurement return signal is received by the first sensing electrode.

Thus, in one aspect of the invention, the method may include locating a target object, such as a tumor, fibroid, tissue, or another other portion of a patient's anatomy for which ablation or BIA treatment is desired, in an anatomy of the patient by performing bioelectrical impedance analysis (BIA) on the anatomy of the patient, including determining a complex impedance in the patient's anatomy. This may be accomplishing by energizing an electrode with a measurement level of power, as explained above, using one of the apparatuses described above or another apparatus. In some embodiment, the method may include positioning a probe in a desired position for ablating the target object, based on the location of the target object determined by the step of locating the target object.

In some variations, the method may include switching the sensing between different electrode groups during use of the device. The measurement signal may be sent continuously or non-continuously. For example, the measurement signal may be sent at set intervals, at trigger points (e.g., after another action has occurred), or at surgeon-controlled intervals. The measurement signal could be applied as alternating current (AC) or low level direct current (DC). For example, the DC measurement signals may be used in systems that determine a bulk tissue property such as resistance. An AC signal is used when complex impedance is being determined. The ablation signal is typically applied as AC, but could alternatively be applied as DC in some applications. Either signal could be applied with variable voltage or constant voltage. Typically, the ablation signal is applied with AC at about 400-500 kHz, to prevent muscle cramping.

The measurement circuit may provide data for manipulation, and once the data is manipulated, for example, the system may determine an impedance in order to make an estimation regarding device positioning or location/condition of the target object. For example, the system could determine that the probe is in contact with certain tissue and is therefore properly placed (for example, in the middle of a tumor). The factors that the system may analyze may be impedance (reactance and/or phase angle between the output voltage and the output current), the amount of output current flowing through the tissue, resistance, temperature, or a combination thereof.

In a system where remote (patch) electrodes and local electrodes (on the probe) are used, it is contemplated that the method may include comparison of whole body values, segmental values, from device to device (in multiple electrode context), probe to patch electrode (ground pad), and/or on the probe alone to provide information to the user about the tissue state and/or probe position.

Any of the sensing and ablation systems 20A, 120A, 220A, 320A, 420A, 520A, 620A or variations thereof may be used for the method described therein. Accordingly, in some variations, the measurement and ablation electrodes are common, or the same, and in other variations, different electrodes are used for the sensing circuit than for the ablation circuit.

In some variations, the method may include sending a measurement signal, determining an impedance or a bulk tissue property, and then estimating a position of the probe based on the impedance or bulk tissue property. As discussed above, the signal may be sent as an AC signal or, in cases for determining a simple impedance, a DC signal. If the impedance indicates that the probe is not in the desired location, the probe is moved, and the process is repeated until it is determined that the probe is placed in the desired position. Thereafter, a higher ablation signal is sent to cause tissue necrosis.

The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include ail values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. A method of treating a target fibroid or other tumor in a patient using a needle probe including at least one electrode located on the needle probe and using a first return electrode and a second return electrode located remote from the needle probe, the method comprising:
    measuring a bulk tissue property including complex impedance information indicative of a location of at least a portion of the needle probe with respect to the target fibroid or other tumor, the impedance information determined using the at least one electrode located on the needle probe and at least one of the first and second return electrodes located remote from the needle probe;
    providing a user with an indication of the location of at least a portion of the needle probe with respect to the target fibroid or other tumor based on the complex impedance information;
    delivering ablation energy to the target fibroid or other tumor via the needle probe when the needle probe is at a desired location determined using the indication of the location of at least a portion of the needle probe with respect to the target fibroid or other tumor based on the complex impedance information;
    providing the user with an indication of a condition of the target fibroid or tumor based upon the bulk tissue property during or after the delivering ablation energy to the target fibroid or tumor;
    controlling the delivering ablation energy to the target fibroid or other tumor via the needle probe using the indication of the condition of the target fibroid or tumor based on the complex impedance information.

2. The method of claim 1, further comprising restricting delivering ablation energy to the target fibroid or other tumor via the needle probe to when the needle probe is at a desired location determined using the indication of the location of at least a portion of the needle probe with respect to the target fibroid or other tumor based on the complex impedance information.

3. The method of claim 1, further comprising:
    repeating measuring the bulk tissue property until the indication of location meets at least one desired location criterion; and
    enabling delivering ablation energy to the target fibroid or other tumor via the needle probe in response to the indication of the location meeting the at least one desired position criterion.

* * * * *